US009005121B2

(12) United States Patent
Addington et al.

(10) Patent No.: US 9,005,121 B2
(45) Date of Patent: *Apr. 14, 2015

(54) SYSTEM AND METHOD OF TESTING THE GASTRIC VALVE AND URETHRAL SPHINCTER

(75) Inventors: W. Robert Addington, Melbourne Beach, FL (US); Stuart P. Miller, Indialantic, FL (US); Robert E. Stephens, Parkville, MO (US)

(73) Assignee: Pneumoflex Systems, LLC, Melbourne, FL (US)

( * ) Notice: Subject to any disclaimer, the term of this patent is extended or adjusted under 35 U.S.C. 154(b) by 546 days.

This patent is subject to a terminal disclaimer.

(21) Appl. No.: 13/456,841

(22) Filed: Apr. 26, 2012

(65) Prior Publication Data

US 2012/0277547 A1 Nov. 1, 2012

Related U.S. Application Data

(60) Provisional application No. 61/480,625, filed on Apr. 29, 2011, provisional application No. 61/533,389, filed on Sep. 12, 2011.

(51) Int. Cl.
G06F 19/00 (2011.01)
A61B 5/00 (2006.01)
(Continued)

(52) U.S. Cl.
CPC .......... *A61B 5/20* (2013.01); *A61B 5/7282* (2013.01); *G06F 19/34* (2013.01); *A61B 5/04882* (2013.01); *A61B 5/0816* (2013.01); *A61B 5/0823* (2013.01); *A61B 5/113* (2013.01); *A61B 5/202* (2013.01); *A61B 5/227* (2013.01); *A61B 5/4211* (2013.01); *A61B 5/4884* (2013.01);

(Continued)

(58) Field of Classification Search
None
See application file for complete search history.

(56) References Cited

U.S. PATENT DOCUMENTS 4,168,703 A * 9/1979 Kenigsberg ................ 600/561
6,354,991 B1 3/2002 Gross et al.
(Continued)

FOREIGN PATENT DOCUMENTS

JP 2010201128 9/2010
WO WO 2007079271 A2 * 7/2007 ............... A61B 5/03
WO WO 2007081626 A2 * 7/2007 ............... A61B 5/07

OTHER PUBLICATIONS

Thompson et al. "Detection of gastroesophageal reflux: value of barium studies compared with 24-hr pH monitoring" American Journal of Roentgenology, vol, 162, No. 3, pp. 621-626; Mar. 1, 1994.
(Continued)

Primary Examiner — William Thomson
Assistant Examiner — Davin Sands
(74) Attorney, Agent, or Firm — Allen, Dyer, Doppelt, Milbrath & Gilchrist, P.A.

(57) ABSTRACT

A system and method tests the gastric valve and urethral sphincter in a patient. A contrast agent is administered into the esophagus of a patient followed by inducing an involuntary reflex cough epoch within the patient to isolate the gastric valve from the lower esophageal sphincter (LES) and isolate the external urethral sphincter from the internal urethral sphincter. An imaging sensor detects the flow of the contrast agent during the involuntary reflex cough epoch and determines whether stomach reflux occurred indicative of a malfunctioning gastric valve. A determination is made if urine leakage occurs indicative of stress urinary incontinence (SUI).

27 Claims, 30 Drawing Sheets

(51) Int. Cl.
*A61B 5/20* (2006.01)
*A61B 5/0488* (2006.01)
*A61B 5/113* (2006.01)
*A61B 5/22* (2006.01)
*A61B 6/00* (2006.01)
*A61B 5/03* (2006.01)
*A61B 5/08* (2006.01)
*A61M 15/00* (2006.01)

(52) U.S. Cl.
CPC ............... *A61B5/6852* (2013.01); *A61B 6/481* (2013.01); *A61B 2562/0247* (2013.01); *A61M 15/009* (2013.01); *A61M 2209/06* (2013.01); *A61B 5/03* (2013.01); *A61B 5/08* (2013.01)

(56) References Cited

U.S. PATENT DOCUMENTS

| | | | |
|---|---|---|---|
| 6,743,165 B2 | 6/2004 | Mosel et al. | |
| 6,896,651 B2 | 5/2005 | Gross et al. | |
| 7,052,453 B2 | 5/2006 | Presthus et al. | |
| 7,179,219 B2 | 2/2007 | Matlock | |
| 7,317,949 B2 | 1/2008 | Morrison et al. | |
| 7,407,480 B2 | 8/2008 | Staskin et al. | |
| 7,483,755 B2 | 1/2009 | Ingle et al. | |
| 7,536,225 B2 | 5/2009 | Spraker et al. | |
| 7,686,760 B2 | 3/2010 | Anderson et al. | |
| 7,753,839 B2 | 7/2010 | Siegel et al. | |
| 8,195,296 B2 | 6/2012 | Longhini et al. | |
| 8,332,041 B2 | 12/2012 | Skelton et al. | |
| 2004/0181161 A1* | 9/2004 | Addington et al. | 600/529 |
| 2005/0065450 A1* | 3/2005 | Stuebe et al. | 600/547 |
| 2005/0265978 A1* | 12/2005 | Chancellor et al. | 424/93.7 |
| 2005/0288603 A1* | 12/2005 | Goping | 600/561 |
| 2007/0185371 A1* | 8/2007 | Bortolotti | 600/29 |
| 2007/0225576 A1* | 9/2007 | Brown et al. | 600/301 |
| 2008/0077043 A1* | 3/2008 | Malbrain et al. | 600/547 |
| 2009/0012350 A1* | 1/2009 | Tihon | 600/30 |
| 2009/0124937 A1* | 5/2009 | Parks | 600/593 |
| 2010/0076254 A1* | 3/2010 | Jimenez et al. | 600/30 |
| 2011/0040211 A1 | 2/2011 | Addington et al. | |
| 2011/0054272 A1* | 3/2011 | Derchak | 600/301 |
| 2011/0060215 A1* | 3/2011 | Tupin et al. | 600/425 |

OTHER PUBLICATIONS

G. Lose "Urethral pressure and power generation during coughing and voluntary contraction of the pelvic floor in females with genuine stress incontinence" British Journal of Urology (1991) pp. 580-585.
Koike et al. "Pathophysiology of urinary incontinence in murine models" International Journal of Urology (2013) pp. 64-71.
Lose et al. "Initial Urethral pressure increase during stress episodes in genuine stress incontinent women" British Journal of Urology (1992) pp. 137-140.
Thind et al. "The effect of bilateral pudendal blockade on the adjunctive urethral closure forces in healthy females" Scand J Urol Nephrol 28: (1994) pp. 249-255.
Kamo et al. "Urethral closure mechanisms under sneeze0induced stress condition in rats: a new animal model for evaluation of stress urinary incontinence" Am J Physiol Regul Integr Comp Physiol, (2003) pp. 359-365.
Kim et al. "Current trends in the management of post-prostatectomy incontinence" Korean Journal of Urology (2012) 53; pp. 511-518.
Rattan et al. "Neural control of the lower esophageal sphincter" The Journal of Clinical Investigation, vol. 54; 10/74: pp. 899-906, (1974).
Mittal et al. "Electrical and mechanical activity in the human lower esophageal sphincter during diaphragmatic contraction" J. Clin. Invest. vol. 81, 4/81; pp. 1182-1189, (1988).
Huang et al. "Conventional weaning parameters do not predict extubation outcome in intubated patients requiring prolonged mechanical ventilation" Respitory Care Paper in Press: Jan. 8, 2013; pp. 1-32.
Tomori et al. "Reversal of functional disorders by aspiration, expiration, and cough reflexes and their voluntary counterparts Frontiers in Physiology" vol. 3, Dec. 2012; pp. 1-14.

* cited by examiner

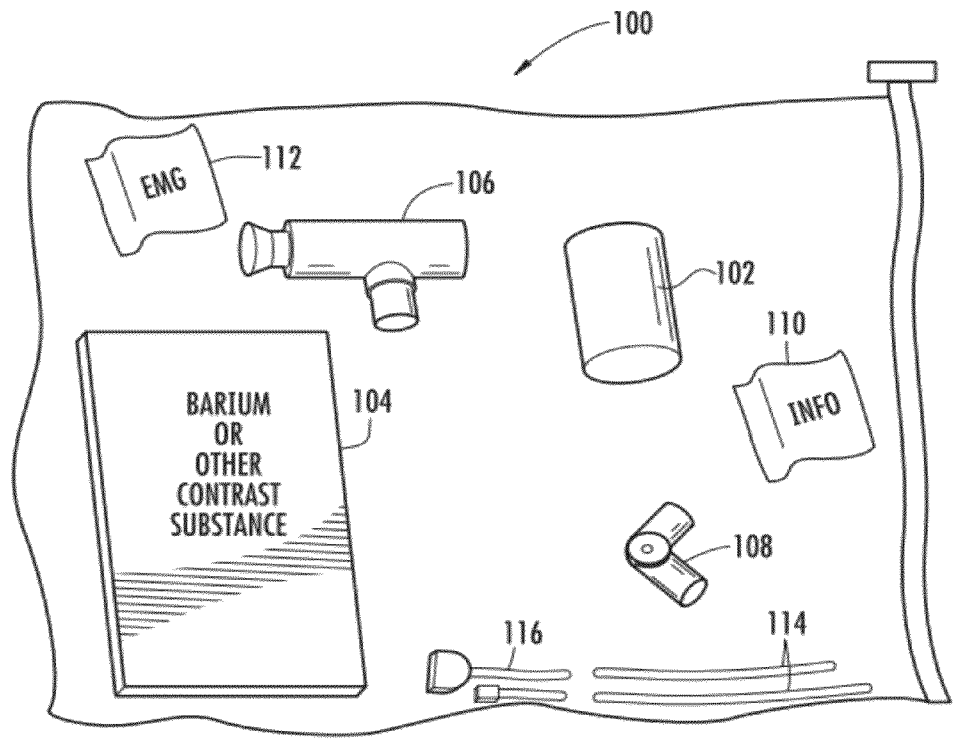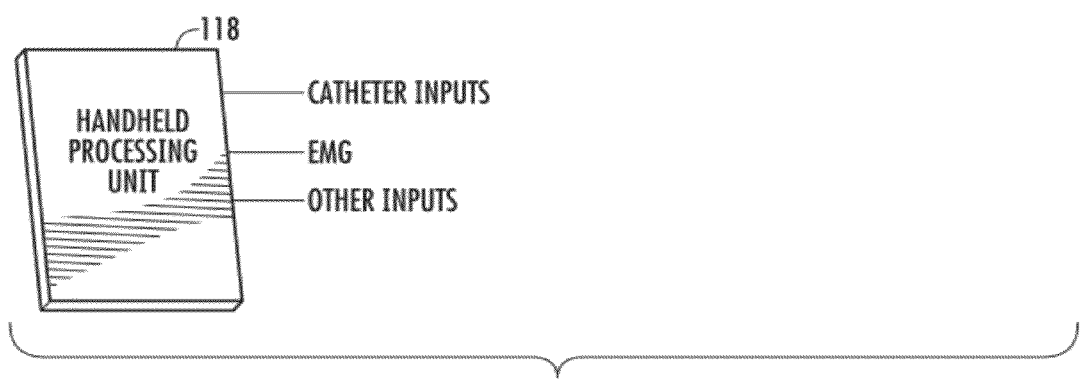
FIG. 3A

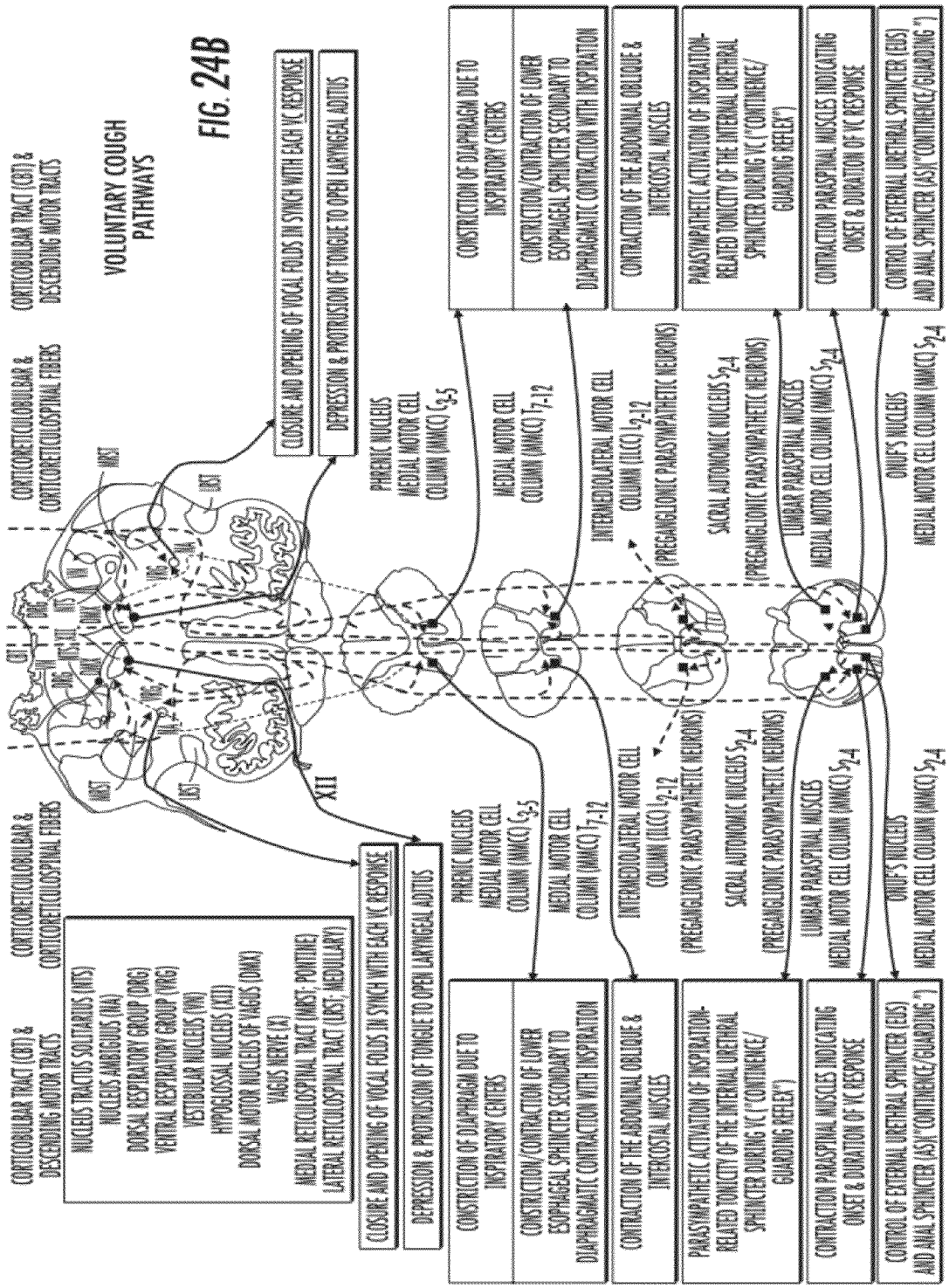

SYSTEM AND METHOD OF TESTING THE GASTRIC VALVE AND URETHRAL SPHINCTER

RELATED APPLICATION(S)

This application is based upon U.S. provisional application Ser. No. 61/480,625 filed Apr. 29, 2011 and U.S. provisional application Ser. No. 61/533,389 filed Sep. 12, 2011, the disclosures which are hereby incorporated by reference in their entirety.

FIELD OF THE INVENTION

This invention relates to testing the gastric valve in a patient and assessing the functioning of a patient's gastric valve and external urethral sphincter using an involuntary reflex cough test.

BACKGROUND OF THE INVENTION

Commonly assigned U.S. application Ser. No. 13/354,100 filed Jan. 19, 2012 by the same inventors, the disclosure which is hereby incorporated by reference in its entirety, discloses a system and method of diagnosing acid reflux using an involuntary reflex cough test. In one example as disclosed, a nasogastric/orogastric (Ng/Og) device is inserted into the stomach and the involuntary reflex cough epoch induced. The intra-abdominal pressure and elevational reflux along the Ng/Og device is measured. In an example, the functional status of the gastric valve is determined based on the measured intra-abdominal pressure and elevational reflux along the catheter. This is a limited analysis that is not always accurate to determine whether there is a reflux problem, requiring an Ng/Og device, which in some cases can interfere with the gastric valve and the lower esophageal sphincter. In another example, an Ng/Og device with an esophageal cuff is used with a sequence of steps, such as inflating a cuff, inducing the involuntary reflex cough epoch, determining if acid reflux has occurred, deflating the esophageal cuff, and again inducing the involuntary reflex cough epoch. Results can be used to determine the functional status of the gastric valve. This is a limited type of test that has not always been found advantageous.

Use of the involuntary reflex cough test with or without a voluntary cough test is also disclosed in commonly assigned U.S. patent application Ser. No. 11/608,316 filed Dec. 8, 2006; Ser. No. 11/550,125 filed Oct. 17, 2006; Ser. No. 12/643,134 filed Dec. 21, 2009; Ser. No. 12/643,251 filed Dec. 21, 2009; Ser. No. 12/878,257 filed Sep. 9, 2010; Ser. No. 12/878,281 filed Sep. 9, 2010; and Ser. No. 12/878,316 filed Sep. 9, 2010; the disclosures which are all hereby incorporated by reference in their entirety. The '257, '281 and '316 applications disclose oral-esophageal-gastric devices, some with esophageal cuffs and/or reflux measurement systems that can be used to assess GERD or determine stress urinary incontinence in some examples using the involuntary reflex cough tests alone or in combination with the voluntary cough test.

In one current test used to determine gastric reflux, fluoroscopy is used. A clinician or doctor will conduct a radiology sweep and use fluoroscopy, also termed video fluoroscopy. A patient swallows a barium drink, for example, containing barium sulphate, typically about 500 to about 1,000 milliliters. The patient lays on a table and the pictures are taken. Often, a tablet or drink is ingested, also termed a fizzy, to produce gas, which acts similar to Alka-Seltzer. Thus, the barium and gas exists in the stomach. Often the patient will lay on their left or right side or the clinician will tilt the patient over such that the head is down. At this point, it is possible to determine if there is acid reflux (or stomach back-up into the esophagus) by viewing the barium. In that respect, the clinician is testing the gastric valve, but the clinician also often claims they are also testing the lower esophageal sphincter (LES). Practitioners have found that test confusing and note reliable indicators are required to determine competency of the gastric valve relative to the lower esophageal sphincter (LES).

SUMMARY OF THE INVENTION

A system and method tests the gastric valve and urethral sphincter in a patient. A contrast agent is administered into the esophagus of a patient followed by inducing an involuntary reflex cough epoch within the patient to isolate the gastric valve from the lower esophageal sphincter (LES) and isolate the external urethral sphincter from the internal urethral sphincter. An imaging sensor detects the flow of the contrast agent during the involuntary reflex cough epoch and determines whether stomach reflux occurred indicative of a malfunctioning gastric valve. A determination is made if urine leakage occurs indicative of stress urinary incontinence (SUI).

The flow of contrast agent can be detected at the level of the LES using a fluoroscopic instrument configured to image the contrast agent. A chemo-irritant can induce the involuntary reflex cough epoch using a nebulizer. Barium sulfate is a preferred contrast agent that is swallowed by the patient. Typically, the involuntary reflex cough epoch is induced immediately following the administration of that contrast agent.

In another example, a urinary catheter having a pressure sensor is inserted within the bladder. An EMG is obtained from the involuntary cough activated intercostals and the data processed from the pressure sensor with the EMG to estimate the severity of the SUI. The EMG can be obtained from the paraspinals.

In another example, the amount of reflux that occurs during the involuntary reflex cough epoch is measured to estimate the severity of the malfunctioning gastric valve. The amount of reflux can be measured during the involuntary reflex cough epoch using a Ng/Og catheter. It is also possible to measure the amount of reflux that occurs during the involuntary reflex cough epoch by comparing a plurality of photomontages taken by the image sensor during the involuntary reflex cough test.

BRIEF DESCRIPTION OF THE DRAWINGS

Other objects, features and advantages of the present invention will become apparent from the detailed description of the invention which follows, when considered in light of the accompanying drawings in which:

FIG. 3A is a fragmentary view of an example of a kit having components for use with the methodology described relative to FIGS. 1 and 2 in accordance with a non-limiting example.

FIGS. 24A and 243 are graphs detailing what occurs during LER with intrinsic sphincter activity (FIG. 24A) and voluntary cough pathways (FIG. 24B).

DETAILED DESCRIPTION OF THE PREFERRED EMBODIMENTS

Different embodiments will now be described more fully hereinafter with reference to the accompanying drawings, in which preferred embodiments are shown. Many different forms can be set forth and described embodiments should not be construed as limited to the embodiments set forth herein. Rather, these embodiments are provided so that this disclosure will be thorough and complete, and will fully convey the scope to those skilled in the art.

Research on the LES and gastric valve indicates there is a problem often with the gastric valve and there is a need for a more ready test to assess the competency of the gastric valve. In accordance with a non-limiting example, the involuntary maneuver, i.e., the involuntary cough test is employed, such as described in the copending and commonly assigned U.S. patent applications identified above.

Figure 1:
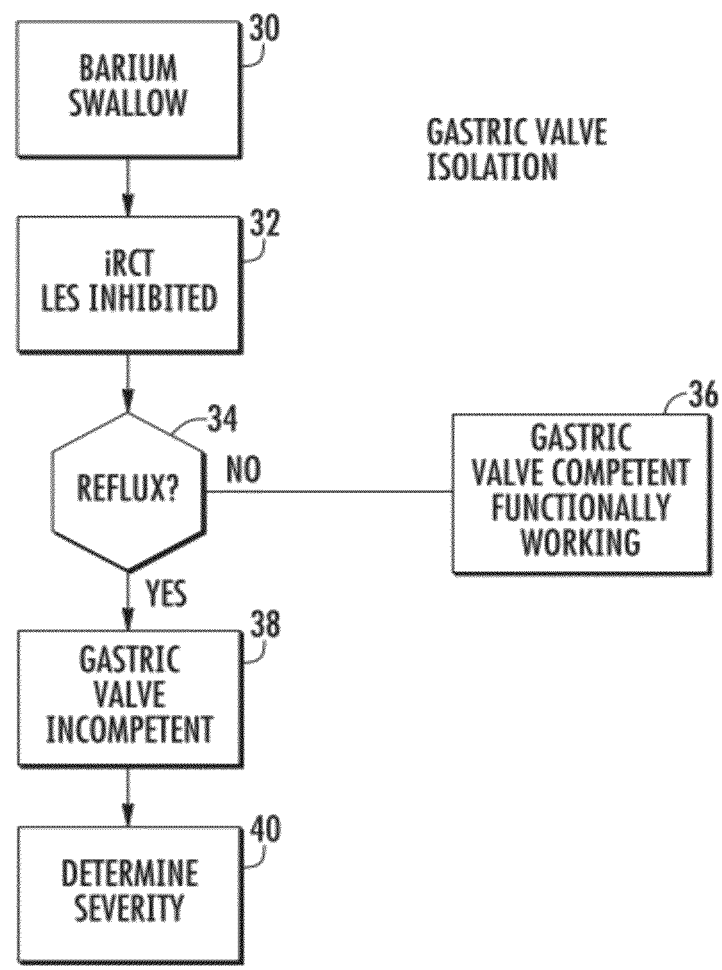
FIG. 1 is a flowchart illustrating a sequence of steps for isolating the gastric valve to assess its function in accordance with a non-limiting example.

FIG. 1 is a flowchart showing a general sequence of steps that can be used for isolating the gastric valve and determine if the gastric valve is competent and functioning adequately in one example. The kit shown in FIG. 3A can include the components for use with this methodology described relative to FIG. 1 and be used with the test system shown in FIG. 3B as explained below.

The sequence begins with a barium swallow (block 30) immediately followed by the involuntary reflex cough test, i.e., iRCT, such as by inhaling a chemo-irritant such as L-tartrate through a nebulizer in one non-limiting example (block 32). The involuntary reflex cough test isolates the gastric valve from the LES. A determination is made using video fluoroscopy, for example, if the reflux has occurred (block 34). If not, the gastric valve is competent and correctly functioning (block 36). If reflux occurs, then the gastric valve is incompetent and is malfunctioning since it is allowing the reflux (block 38). It is possible to determine the severity of the reflux (block 40), for example, by measuring the amount of reflux that occurs during the involuntary reflex cough epoch to estimate the severity of the malfunctioning gastric valve. This can be accomplished using enhanced fluoroscopy or using a Ng/Og catheter located at the LES or other location as later described to determine the extent of reflux.

Figure 2:
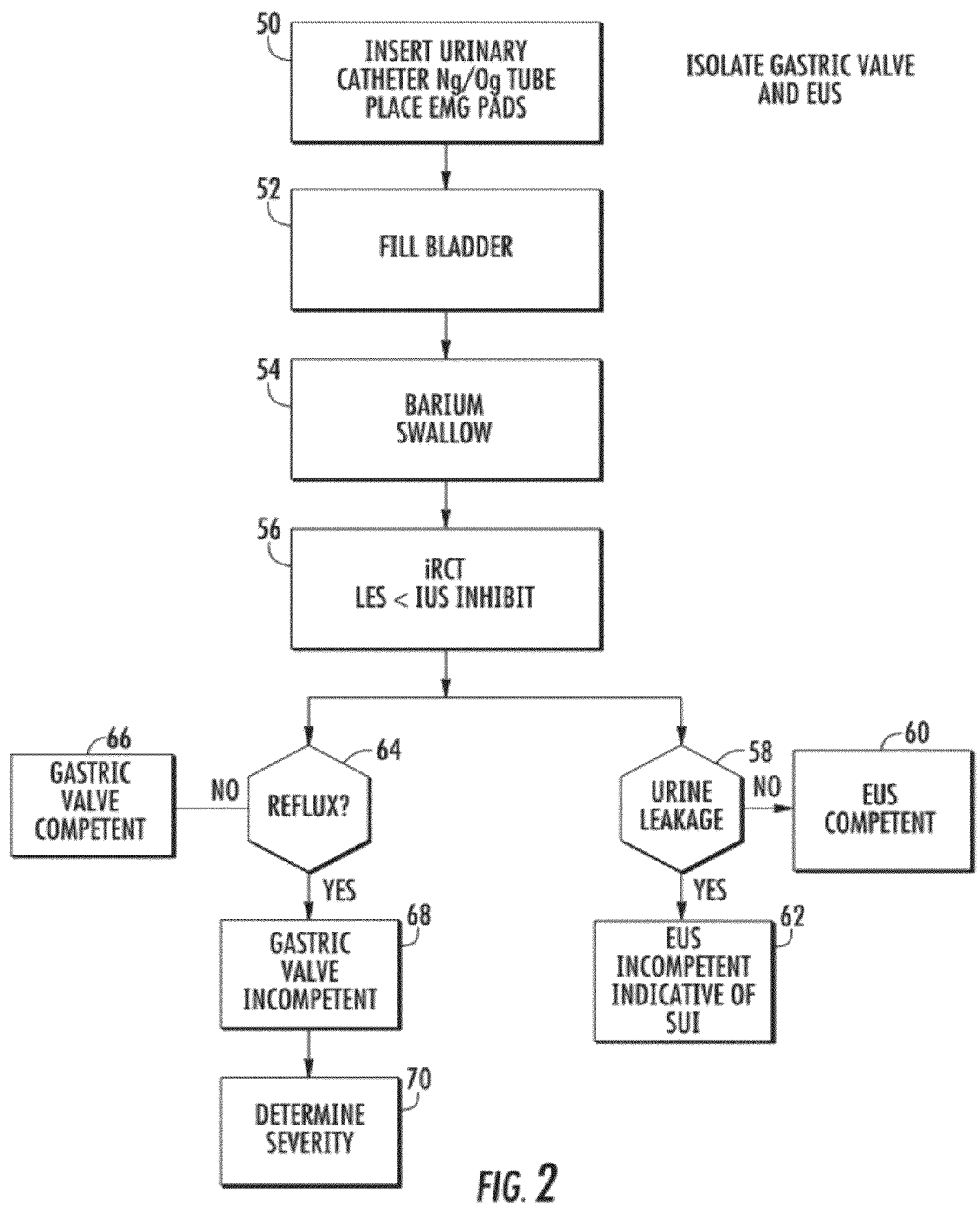
FIG. 2 is another flowchart illustrating a sequence of steps for isolating the gastric valve and external urethral sphincter to assess their function in accordance with a non-limiting example.

FIG. 2 is another flowchart showing a sequence of steps used for assessing the competency of the gastric valve and isolating the gastric valve from the LES and also isolating the external urethral sphincter from the internal urethral sphincter to determine stress urinary incontinence.

The process begins by inserting a urinary catheter in the patient with a pressure sensor in one example and a sensor located at the internal urethral sphincter in an example. The Ng/Og tube may include at least one sensor to be positioned at the LES and pH sensor at different positions. EMG pads can also be positioned at appropriate locations at the mid-axillary line of the T7-8 internal space (block 50). This could also include the paraspinals. The bladder is filled such as with saline solution (block 52). Barium or other contrast material is swallowed (block 54) and the involuntary reflex cough test induced (block 56). Two analysis paths are shown. A determination is made whether urine leakage occurred (block 58). If not, then the external urethral sphincter is competent and functioning adequately (block 60). If yes, then the external urethral sphincter leaked indicative of stress urinary incontinence (SUI) (block 62). Some determination of the severity of SUI or other problems can possibly be determined through analyzing the EMG results together with any intra-abdominal pressure that has been recorded during the involuntary reflex cough epoch. Reference is also made to the incorporated by reference applications for appropriate data and analysis regarding same. A determination is also made whether reflux occurred (block 64). If not, then the gastric valve is competent and functioning adequately (block 66). If yes, then the gastric valve is incompetent and is not functioning correctly (block 68). By using a Ng/Og tube or advanced imaging of the contrast agent, e.g., Barium Sulfate, it is possible to determine the severity of the reflux (block 70) such as measuring the amount of reflux at the LES and other locations within the esophagus.

A patient kit for assessing the gastric valve in conjunction with fluoroscopy and the EUG can be provided and an example is shown in FIG. 3A at 100. Items in this illustrated kit include:

1) Pneumoflex or USA Flex 20% tartaric acid in 3 ml unit dose vial 102;
2) 1000 ml Barium sulfate USP 104;
3) Ion Nebulizer or Crossfire Nebulizer 106;
4) Swivel adapter for nebulizer 108;
5) Protocol information sheet 110;
6) EMG pads 112;
7) Ng/Og tube or catheter 114; and
8) Urinary catheter 116.

The purpose of this kit 100 is to simplify the assessment of the gastric valve functioning (and/or external urethral sphincter) using the involuntary maneuver, i.e., involuntary reflex cough test (iRCT) to increase the intra-abdominal pressure to isolate the gastric valve while inhibiting the LES and, in some examples, isolating the external urethral sphincter. Evidence of gastric reflux can be observed directly using video fluoroscopy and evidence of SUI determined by isolating the external urethral sphincter to determine when there is urine leakage.

As shown in FIG. 3A, a handheld processing unit, such as described later relative to FIGS. 21 and 22, can be associated with the kit 100 and includes catheter inputs, EMG and other inputs.

It is well known that the gastric valve allows food to enter the stomach but prohibits reflux of gastric acid into the esophagus. As to the patient kit 100, one aspect is the use of the swivel adapter 108 for the nebulizer such that when the patient is turned over, the nebulizer through use of the swivel adapter can be more readily used by a doctor.

There have been a number of previous tests to distinguish different urinary incontinence problems including: 1) increasing the intra-abdominal pressure using a Valsalva maneuver; 2) having the patient jump up and down; or 3) generating one or more strong voluntary coughs. Through much clinical work, such as described herein and in the copending and incorporated by reference patent applications identified above, it has been determined that the involuntary reflex cough test (iRCT) activates the nucleus ambiguus, as compared to the voluntary reflex cough test.

Figure 3B:
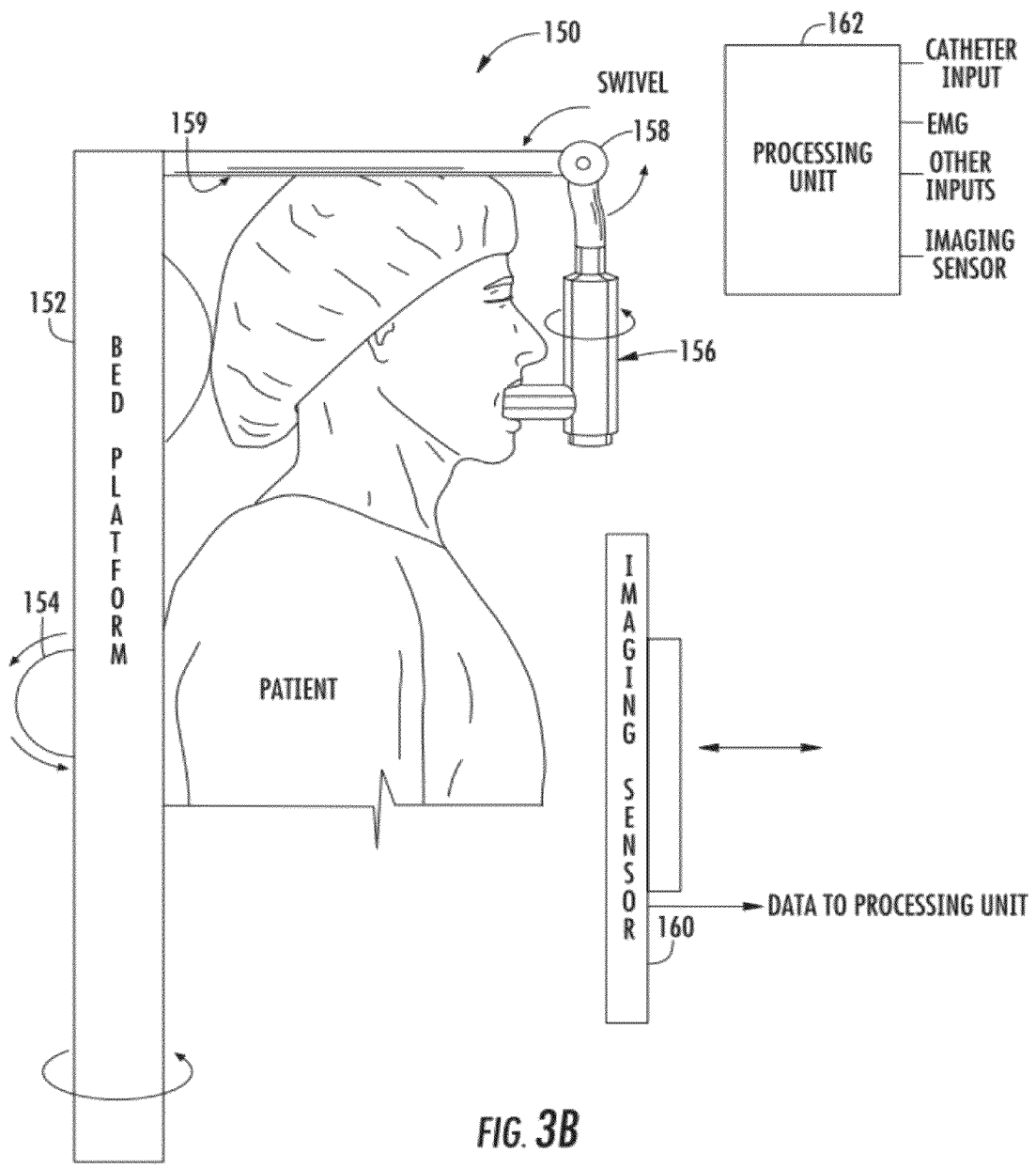
FIG. 3B is a view showing a system that includes a patient bed as a platform and imaging sensor for performing the methodology of FIGS. 1 and 2.

FIG. 3B shows a patient examining system 150 for imaging any contract agent that can be used to implement the methodology as described. The patient examining system includes a bed 152 supported on a swivel/pivot 154 that is typically motor driven and allows the bed to be rotated and pivoted to place the patient in any predetermined position as inclined or turned over, if necessary. A nebulizer 156 is supported on a swivel adapter 158 and rotatable into various positions. The nebulizer 156 can be removable and could include a separate canister (shown by dotted lines at 15) or have nebulized medicine fed through a support arm 159 associated with the nebulizer and swivel adapter 158. Imaging sensor 160 can be positioned adjacent the patient for imaging barium or other contrast agent the patient has swallowed (or been forcibly administered depending on whether the patient is conscious). The processing unit 162 includes various inputs as described relative to the processing unit 118. The processing unit 162 can be a handheld processing unit or a fixed computer connected to the imaging sensor and various catheters inserted in the patient. The imaging sensor 160 in one example is a fluoroscopic instrument configured to image the contrasting agent. The imaging sensor is typically connected to the bed and moveable into a position adjacent the patient to image the contrast agent as it flows through the esophagus into the stomach during the involuntary reflex cough epoch. Data is transferred to the data processing unit where the data is processed and the amount of reflux that occurs during the involuntary reflex cough epoch measured to estimate the severity of the malfunctioning gastric valve in one example or the extent of the gastric valve adequate functioning. This could be accomplished, for example, by comparing a plurality of photomontages taken by the image sensor during the involuntary reflex cough test.

Figure 7A:
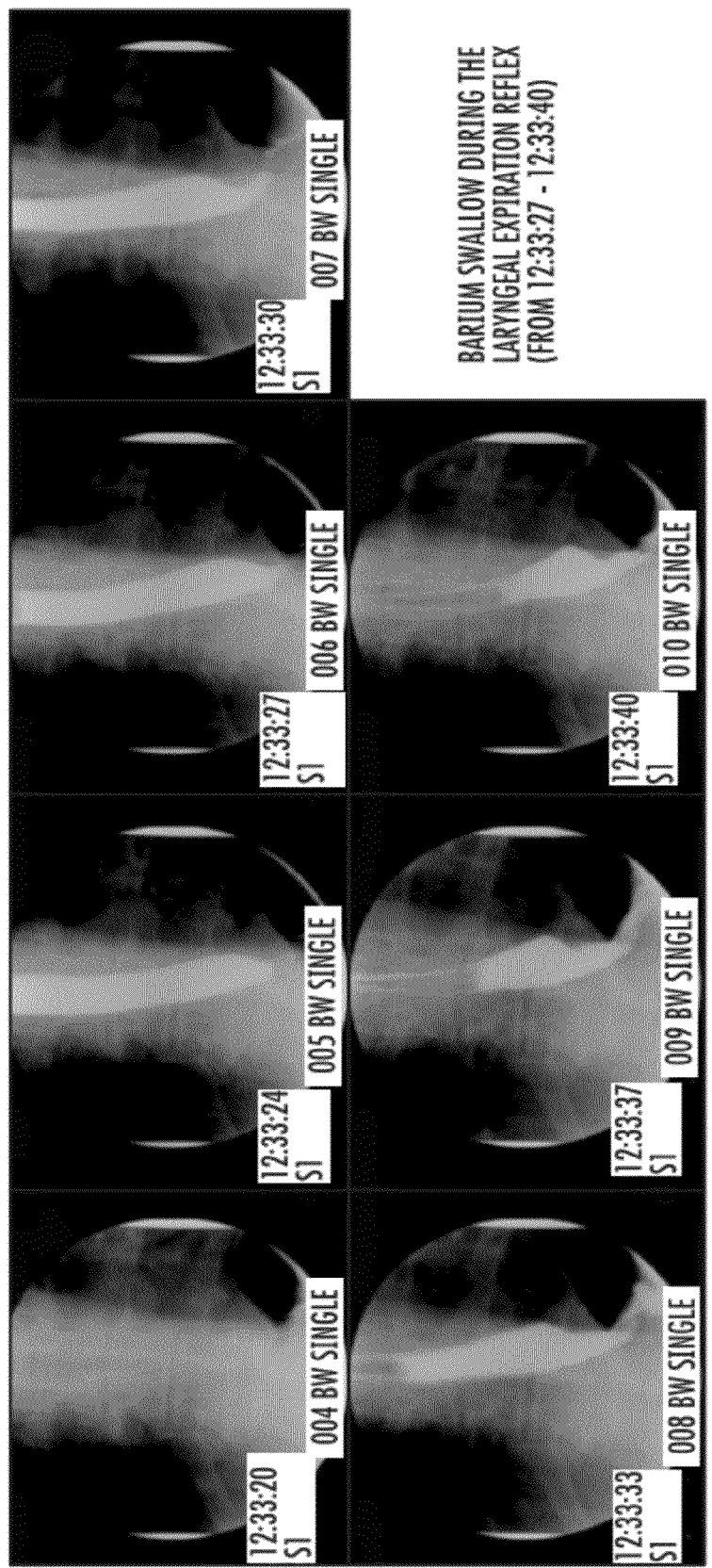
FIG. 7A are images showing the barium swallow during the laryngeal expiration reflex.

It is possible for a series of photomontages to be viewed by a clinician such as those photomontages shown in FIG. 7A and determine the extent of reflux and through experience make an estimate as to the severity of the malfunctioning gastric valve. Also, imaging data can process the photomontages and make an estimate based on various algorithms that could be supplied to the processing unit. Additionally, the amount of reflux that occurs during the involuntary reflex cough epoch can be measured using an Ng/Og catheter that has various pressure sensors and pH sensors along its length from the stomach and gastric valve up to the LES and upward through the esophagus. Greater amounts of reflux would have greater pressure that could be measured. Also, the amount of reflux that rises along the Ng/Og catheter tube would be an estimate of the severity of the malfunctioning gastric valve since greater amounts of reflux would indicate a more severely malfunctioning gastric valve in some examples.

The iRCT selectively activates the Medial Motor Cell Column (MMCC) of the spinal cord rather than the (Lateral) LMCC to fire muscles embryologically predetermined to be involuntary cough activated muscles in the pelvis. In the past in the field of urology, urologists did not selectively activate MMCC without overtly activating the LMCC. Magnetic stimulation or electrical spinal cord stimulation activate both cell columns and thus it is not possible to sort out pathology with these tests. Magnetic stimulation or other approaches from CNS activation set off both columns. The involuntary reflex cough test activates embryologically predetermined muscles for airway protection and continence that travel primarily through the MMCC in the spinal cord.

The laryngeal expiratory reflex (LER) is a brainstem-mediated reflex that initiates an immediate series of expiratory coughs without an inspiratory phase. The LER is the involuntary reflex that neurologically protects the upper airway from noxious aspirants and, as such, it has a critical neurological function, which is unique to humans. The induced reflex cough test (iRCT) can be triggered such as by using a nebulized 20% solution of a mild chemoirritant, such as tartaric acid, to elicit in patients a LER. The iRCT is characterized by a series of, at least, five expiratory reflex coughs (C5) with a typical 17 ms latency to the external abdominal oblique (EAO) muscles. During the LER, contraction of the external abdominal oblique (EAO) muscles compress the abdominal viscera, which push against the relaxed diaphragm superiorly for the expiratory phase and push inferiorly against the urinary bladder and rectum, with a concomitant increase in intra-abdominal pressure (IAP).

Since reflex cough is expiratory and is not preceded by diaphragmatic contraction associated with inspiration, the iRCT indicates the native tonicity and function of the urethral sphincter (US) and lower esophageal sphincter (LES), which is typically critical in the diagnosis of SUI and GERDS, respectively. Animal models cannot adequately study VC and the LER, since the animals are surgically decerebrated and intubated.

The physiological functions of the lower esophageal (LES) and internal urethral sphincters (IUS) change depending on whether there is a voluntary or involuntary respiratory cough maneuver. Clinical trials and testing were accomplished using prospective, barium videofluoroscopy study (BSV) of the LES on 4 healthy adult males during voluntary cough (VC), laryngeal expiration reflex (LER) as an involuntary cough, breath-hold maneuvers and normal inspiration. A subject had fiberoptic pressure catheters placed in the LES and IUS, and EMG recording of the right T7-8 intercostals during respiration. The BSV showed closure and relaxation of the LES corresponding to the inspiration and expiration of VC. BSV showed patency of the LES during the LER. BSV showed closure of the LES during the deep inspiration/breath-hold event. Pressure catheters in the LES and IUS showed increased pressure during inspiration. These observations suggest that pulmonary inspiration afferents elicit a patterned reflex motor response to the LES and IUS, referred to as the inspiration continence reflex (ICR).

The Breuer reflex describes pulmonary inspiration afferent fibers with separate pulmonary expiration afferent fibers. The respiratory cycle is modified in many ways and by many influences that also activate the expiratory muscles for respiration. Breuer found that when the lung was distended by inspiration, pulmonary afferent impulses were conveyed to the brainstem via the vagus nerve and these afferent impulses reflexively initiated expiration. When the lung was deflated, other pulmonary afferent receptors were stimulated and their impulses, also conveyed to the brainstem by the vagus nerve, reflexively initiated the next inspiration. This report was one of the first feedback circuits for reflex self-regulation of respiration in mammals.

Recent clinical trials by the inventors on using voluntary cough (VC) and the laryngeal expiration reflex (LER) have been investigated using these respiratory maneuvers to assess stress urinary incontinence (SUI) in women and neurological airway protection in humans and are set forth. The urodynamic tracings from the SUI clinical trial suggested that the inspiration during VC may stimulate pulmonary afferent fibers that may directly activate closure of the internal urethral sphincter (IUS).

The relationship between inspiration and expiration, and the effects of reflex regulation of respiration on structures such as the internal urethral and lower esophageal sphincters have not been reported in the past. Attention is referred to the articles by: Bishop B, Bachofen H. Comparison of neural control of diaphragm and abdominal muscle activities in the cat. J Appl Physiol 1972; 32:798-805; Bishop B, Bachofen H. Vagal control of ventilation and respiratory muscles during elevated pressures in the cat. J Appl Physiol 1972; 32:103-112; and Breuer J. Die Selbststeuerung der Athmung durch den Nervus vagus. Stitzungsberichte der kaiserlichen Akademie der Wissenschaften Mathematisch-naturwissenschaftliche Classe, Wien 1868; 58:909-937.

However, the analysis of the urodynamic data during the SUI clinical trials using voluntary and involuntary cough maneuvers led to an investigation of the effect of inspiration and expiration on IUS and LES activity of the instant application. It is believed based on clinical trials as described and that during the inspiratory and expiratory components involved in voluntary and involuntary cough and breath-hold maneuvers, the inspiration neurophysiological system, as described by Breuer and Bishop, also controls the IUS and LES function.

A prospective, barium swallow videofluoroscopy (BSV) study and a cohort study of the IUS and LES using fiberoptic pressure catheters was performed. Four normal, healthy male subjects participated in the BSV study and one subject participated in both the BSV and catheter studies. After review of the study protocol, informed consent was obtained from all subjects. BSV studies of the LES were performed, using only thin barium solution, on each subject. The subjects were standing for all BSV test maneuvers using a standing anterior-posterior view. Videofluoroscopic photomontages were captured at 3-second intervals and analyzed for each maneuver.

For the VC, each subject swallowed a small cup of thin barium solution followed immediately by a deep inspiration and a VC. The BSV captured, at the level of the LES, a photomontage of the barium flow during the VC.

The breath-hold maneuver required the subject to perform a deep inspiration and breath-hold followed immediately by swallowing a small cup of thin barium solution. All of the photomontages were visually analyzed to determine the relationship of the barium to the position of the LES and diaphragm.

The induced reflex cough test is a cough provocation test that stimulates the laryngeal expiratory reflex (LER). The LER is a series of expiratory coughs that together form the cough epoch, which occurs without a significant preceding inspiration. This LER cough epoch caused five coughs (C5) with an average duration of 14.8 seconds.

Various components and materials were used to perform the iRCT in this example. These components include a vial containing a 20% solution of tartaric acid such as manufactured by Nephron Pharmaceutical, Inc. of Orlando, Fla.; jet nebulizer; an oxygen flow meter; an oxygen tank; and gloves and safety mask. The jet nebulizer was FDA approved for use in the U.S. and bore the CE Marking designating the manufacturer's compliance with Council Directive 93/68/EEC.

For the BSV study using the iRCT, the subject swallowed a small cup of thin barium solution immediately followed by administration of the iRCT. The BSV captured, at the level of the LES, a photomontage of the flow of the barium during the LER involuntary cough maneuver. The system such as shown in FIG. 3B could be used.

The four subjects had nasogastric and urethral fiberoptic, disposable catheters (#10 and #7 French catheters, respectively in this example) with the sensors placed at the level of the LES and IUS, respectively. Electromyography (EMG) electrodes were placed at the mid-axillary line of the T7-8 intercostal space and were used to confirm the inspiratory activity of the intercostal muscles. A Lumax TS Pro catheter was used to record LES and IUS pressures and EMG activity. However, the handheld unit as described relative to FIGS. 21 and 22 could be used to record all data and process it. All urodynamic (UD) equipment and catheters used in this study were FDA approved for use in the U.S. and bore the CE Marking designating the manufacturer's compliance with Council Directive 93/68/EEC. These components can be sold as a kit and packaged as a system as described before.

The subject was positioned in a semi-recumbent lithotomy position (approximately 60 degrees head up). The subject performed deep and shallow breathing and breath-hold maneuvers with simultaneous recording of LES and IUS pressures, and EMG intercostal inspiratory activity. The recordings were saved on the Lumax TS Pro in this example for analysis of pressure waves and EMG activity.

Figure 4A:
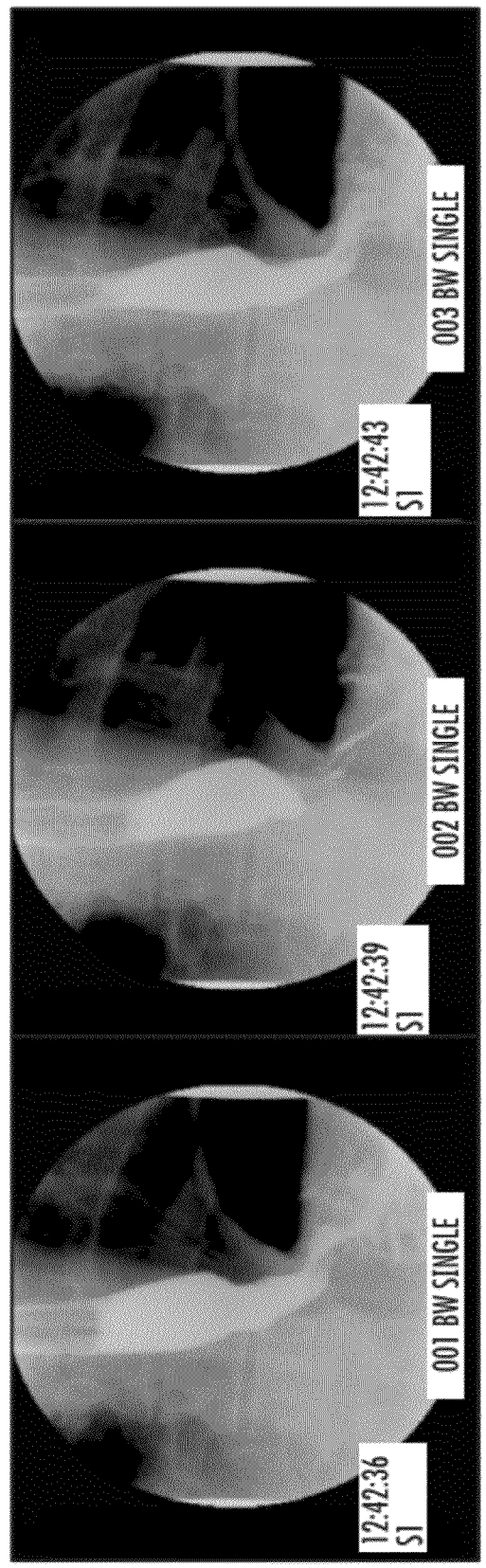
FIG. 4A are images for the inspiration continence reflex (ICR) as part of the involuntary reflex cough test and showing the LES.
Figure 4B:
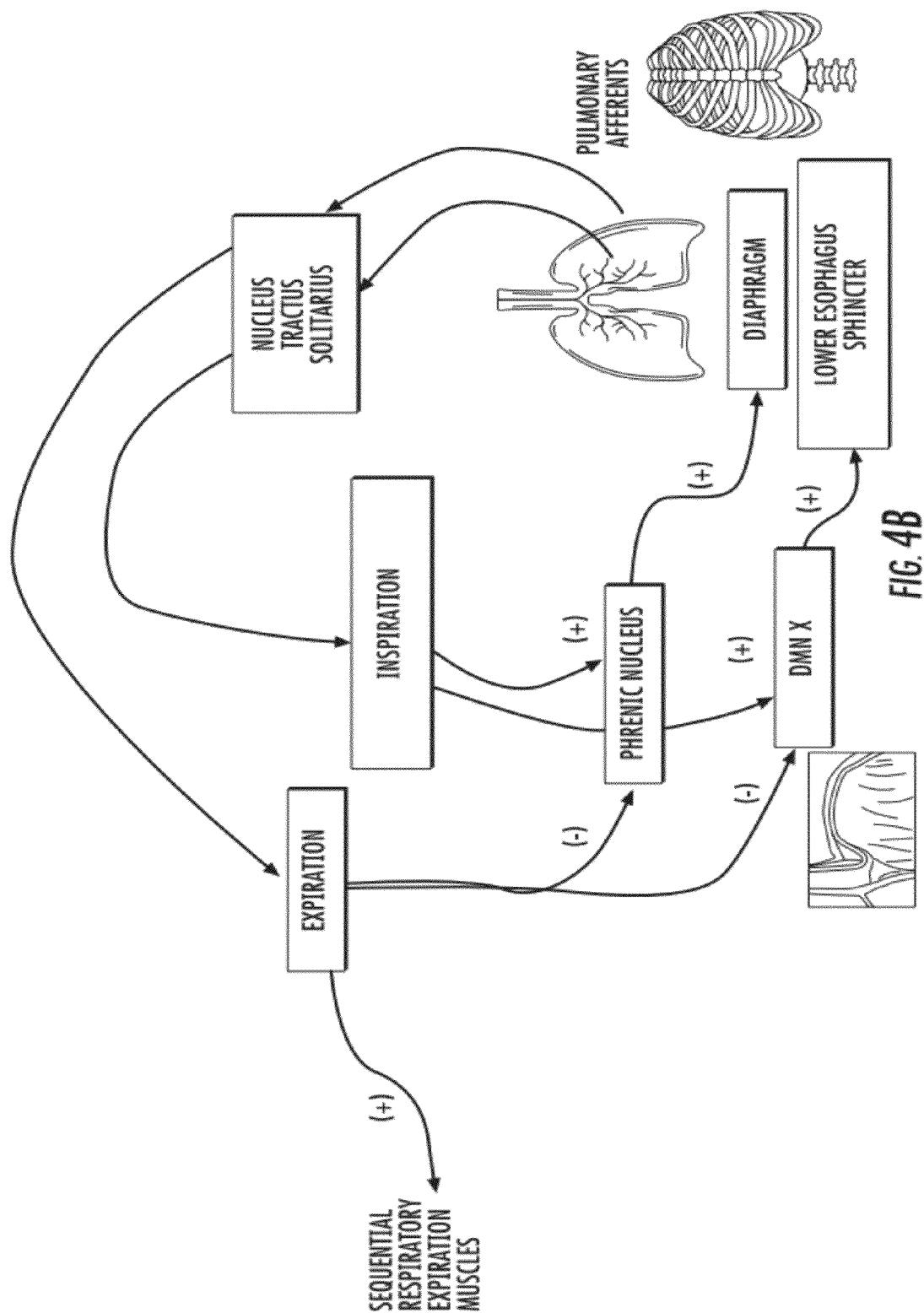
FIG. 4B is a nerve conduction graph showing the inspiration continence reflex.

BSV followed immediately by the VC showed transient interruption of barium at the LES during inspiration, which released with expiration as shown at FIG. 4A. The VC had phases of inspiration, expiration and recovery (shown in the photographs), lasting approximately 6 seconds. This result was reproducible in all subjects. It is believed that the ICR is dependent upon the initiation of the vagal pulmonary inspiration afferent fibers to the Nucleus Tractus Solitarius (NTS) for the activation of the patterned sequence of motor responses elicited by motor nuclei associated with every inspiration. These include the Phrenic, Dorsal Motor and Sacral Autonomic Nuclei, which gives rise to diaphragm activation and the inhalation tonicity closure of the LES and the IUS. This sphincter closure maintains continence, during volitionally elevated IAP events. The pulmonary expiration afferent fibers to the Nucleus Tractus Solitarius (NTS) release the diaphragm activation and the inhalation tonicity closure of the LES and IUS. The sequence above in FIG. 4A is barium swallow (first film) followed immediately by deep inspiration (middle film), which closes the LES and stops the barium (third film). The expiration in voluntary cough releases the LES and allows barium to enter the stomach. The ICR (Inspiration Continence Reflex) event probably occurs with the activation of pulmonary inspiration afferent fibers and the response may vary according to the activation of different motor nuclei depending on the rate and depth of inspiration. FIG. 4B shows a schematic diagram of ICR nerve impulse conduction during voluntary cough and barium swallow and LES.

Figure 5A:
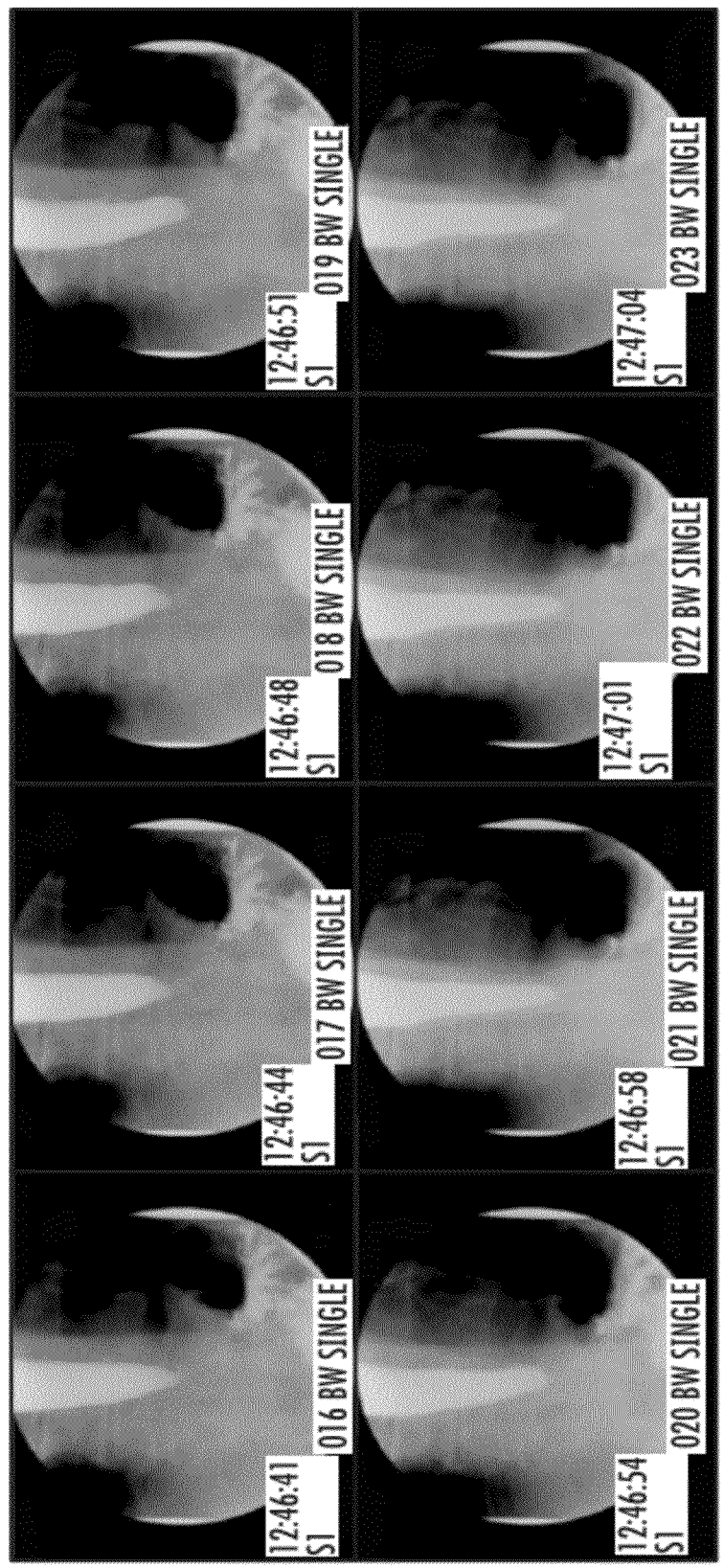
FIG. 5A are images showing a barium swallow during breath-hold.
Figure 5B:
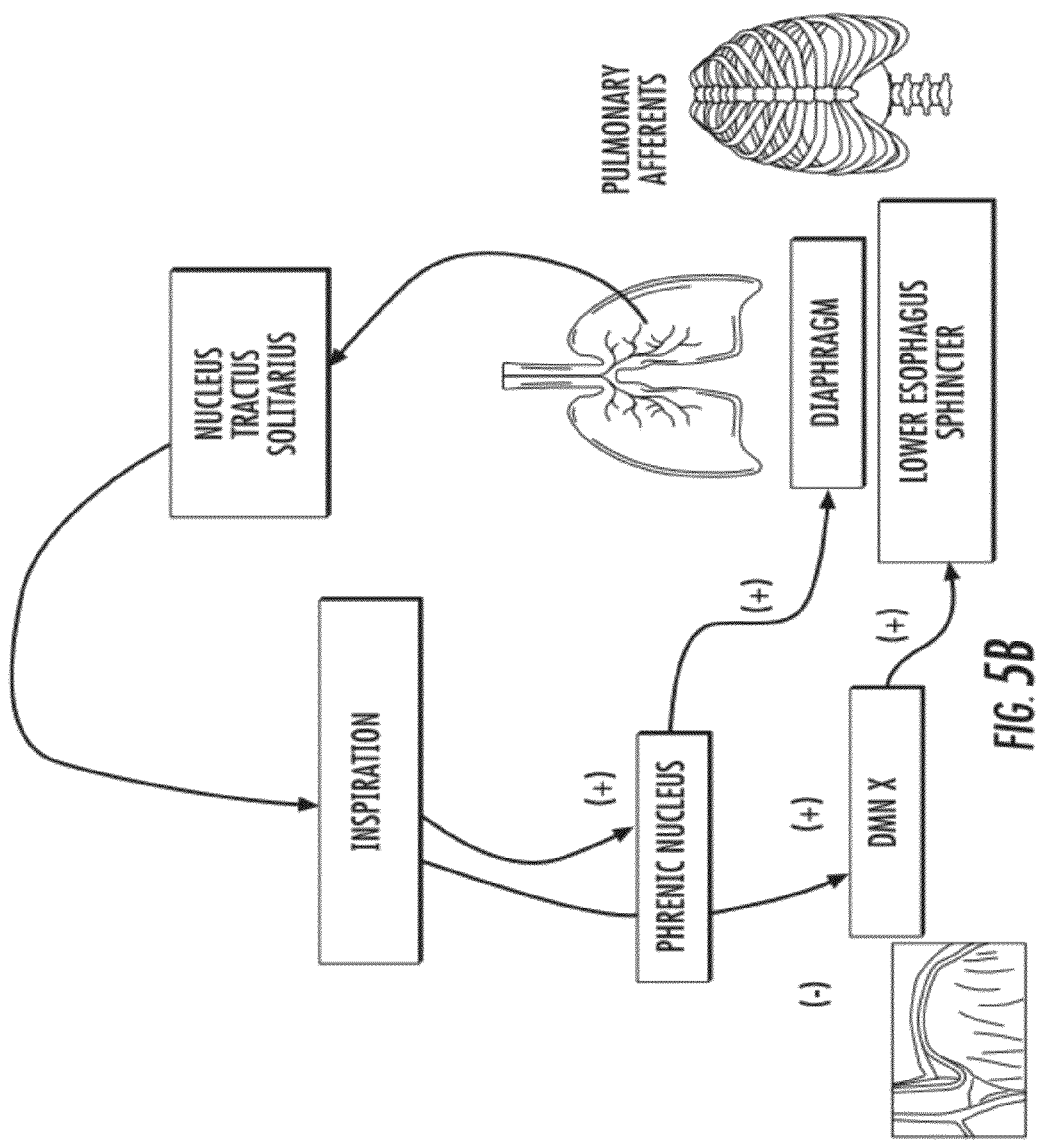
FIG. 5B is a nerve conduction graph for the barium swallow during breath-hold.

Deep inspiration and breath-hold immediately followed by BSV showed complete interruption of barium at the LES during the entire breath-hold event as shown in FIG. 5A. The ICR nerve impulse conduction is demonstrated in the schematic nerve impulse diagram of FIG. 5B and photomontage in FIG. 5A. The photos depict the inspiration followed by swallowing barium. The LES closed with deep inspiration and remains closed during the entire duration of breath-hold (>20 seconds), which appeared to hold the barium above the LES. The barium stayed above the LES until expiration.

Figure 6:
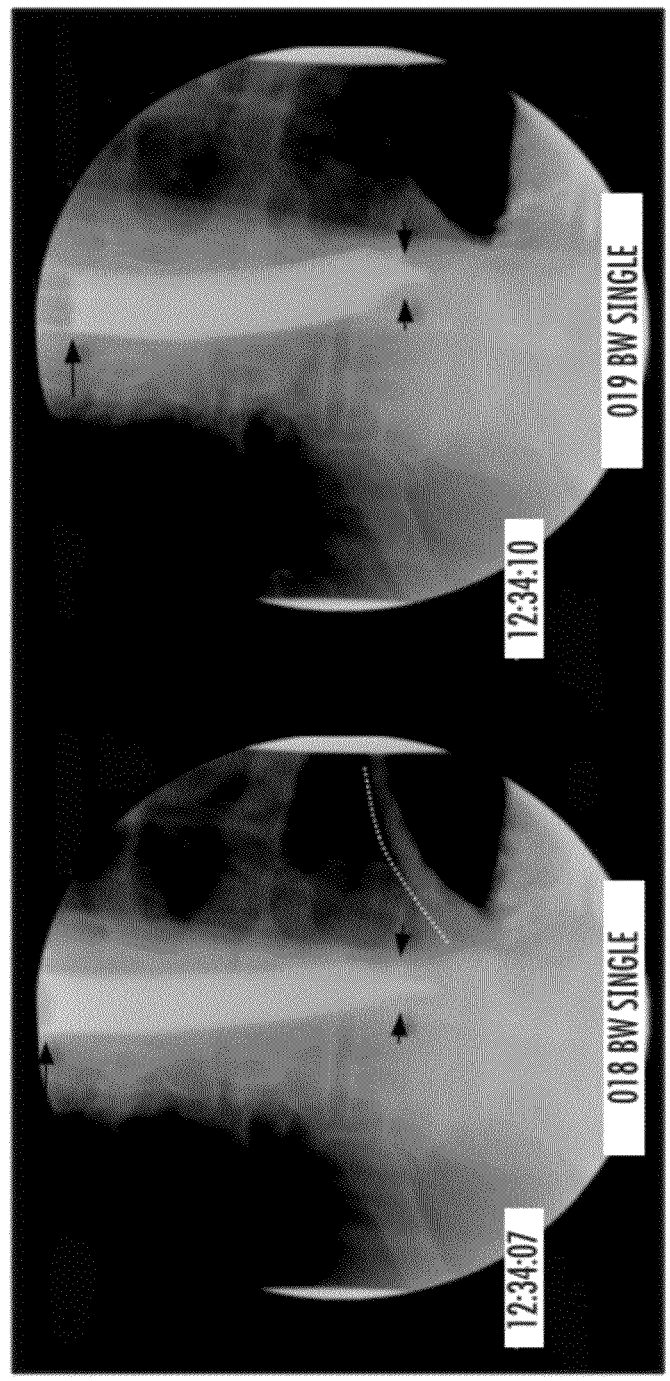
FIG. 6 are images of a barium swallow during breath-hold in the LES.

The photomontage in FIG. 5A had a 23-second duration of and the flow of the barium was completely interrupted at the level of the LES during this entire voluntary maneuver. This result was reproduced in all subjects. In the region of the distal esophagus, diaphragm and proximal stomach are magnified using two consecutive images from a breath-hold montage that are separated by 3 seconds as shown in FIG. 6. This is an enlarged sequence of photos taken during a deep inspiration and breath-hold followed by barium swallow. The diaphragm (dotted line) appears below the level of the barium. It is believed that inspiration tonicity closure of the LES (lower arrowheads) prevented the flow of barium into the stomach. The arrows at the proximal esophagus indicate the level of barium solution. The arrowheads indicate the level of the proximal portion of the LES and the barium solution. The barium in distal esophagus showed a distinctive V-shaped tapering that suggested a cuff-like closure of the LES. The dotted line in FIG. 6 was placed above the apparent diaphragm shadow, which was clearly inferior to the distal tip of the barium solution. This result was reproducible in all subjects.

The BSV followed immediately by the LER activation, using the IRCT, showed no interruption of barium at the LES during expiratory coughs as shown in FIG. 7A. The mucosa of the vestibule of the larynx is innervated by the middle ramus of the internal laryngeal nerve. The central processes of these afferent fibers enter the medulla with the vagus nerve and terminate in restricted regions of the nucleus tractus solitaries (NTS). Stimulation of these laryngeal afferent fibers using a nebulized solution of 20% tartaric acid initiates a series of five expiratory "coughs" without inspiration, i.e., cough epoch, characteristic of the LER. The primary function of the LER is to clear the upper airway when food or fluids have entered the laryngeal vestibule. The LER appears to be inhibitory for inspiration and breathing and the associated reflex motor activations, which prevent closure of the LES during the involuntary cough epoch. Prevention of closure of the LES, during involuntary elevated IAP, may cause reflux of stomach contents in the presence of an incompetent gastric valve. The barium flow in the above standing LER cough epoch does not stop in the photomontage. The LES appears to be patent during the LER cough epoch, which prevents interruption of the flow of barium into stomach. The top record are films taken during an LER showing no closure of the LES. The nerve conduction pathways are shown in FIG. 7B.

The LER photomontage in FIG. 7A had a 13-second duration without an inspiration. The failure of the LES to close during the LER cough epoch with continuous barium flow was reproducible in all subjects.

Figure 8:
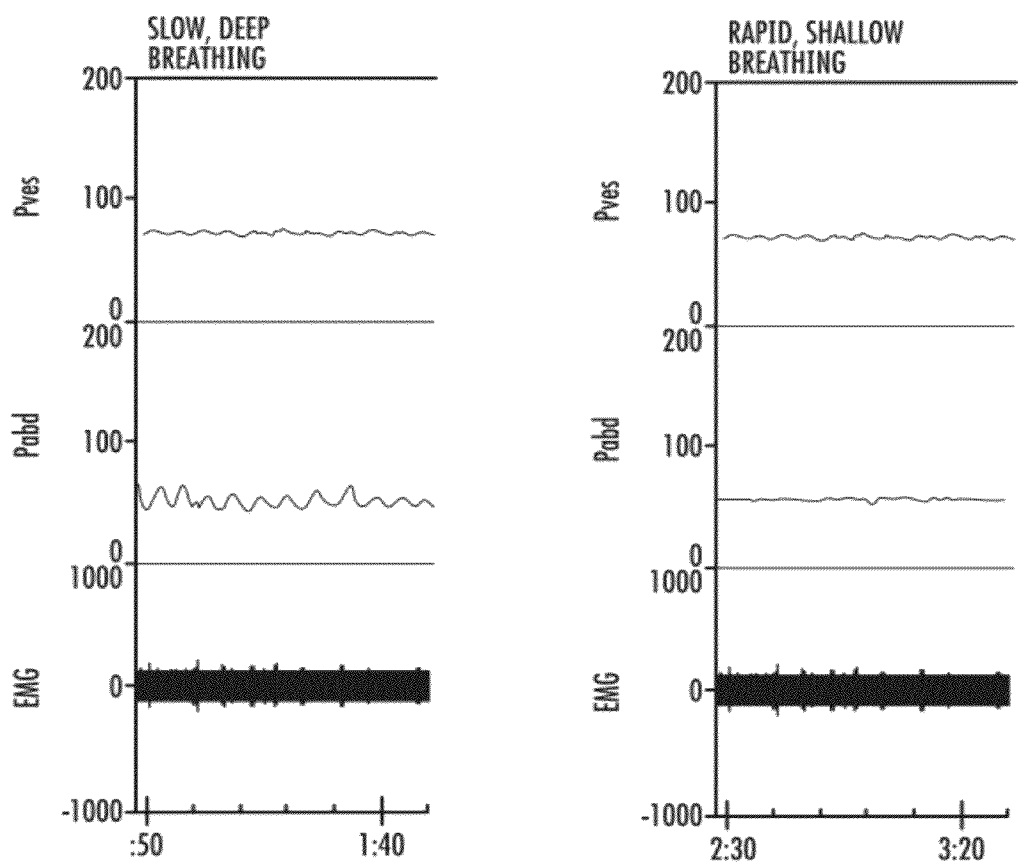
FIG. 8 are graphs showing pressure recordings of the internal urethral sphincter (IUS) and LES that are synchronized with respiration.

In the one subject, who had catheters in the LES and IUS, there were corresponding increases in LES and IUS pressures associated with inspiration as confirmed by intercostals EMG activity as shown in FIG. 8. Inspiration continence reflex occurs as demonstrated by simultaneous pressure recordings of the IUS and LES with respiratory EMG of the intercostal muscles at T7-8 interspace. During slow, deep and rapid, shallow inspiration and expiration, pressure waves indicated the respiratory rate and depth dependent variation. The amplitude of the catheter pressure waves was limited by the sensitivity of the fiberoptic transducers.

Figure 7B:
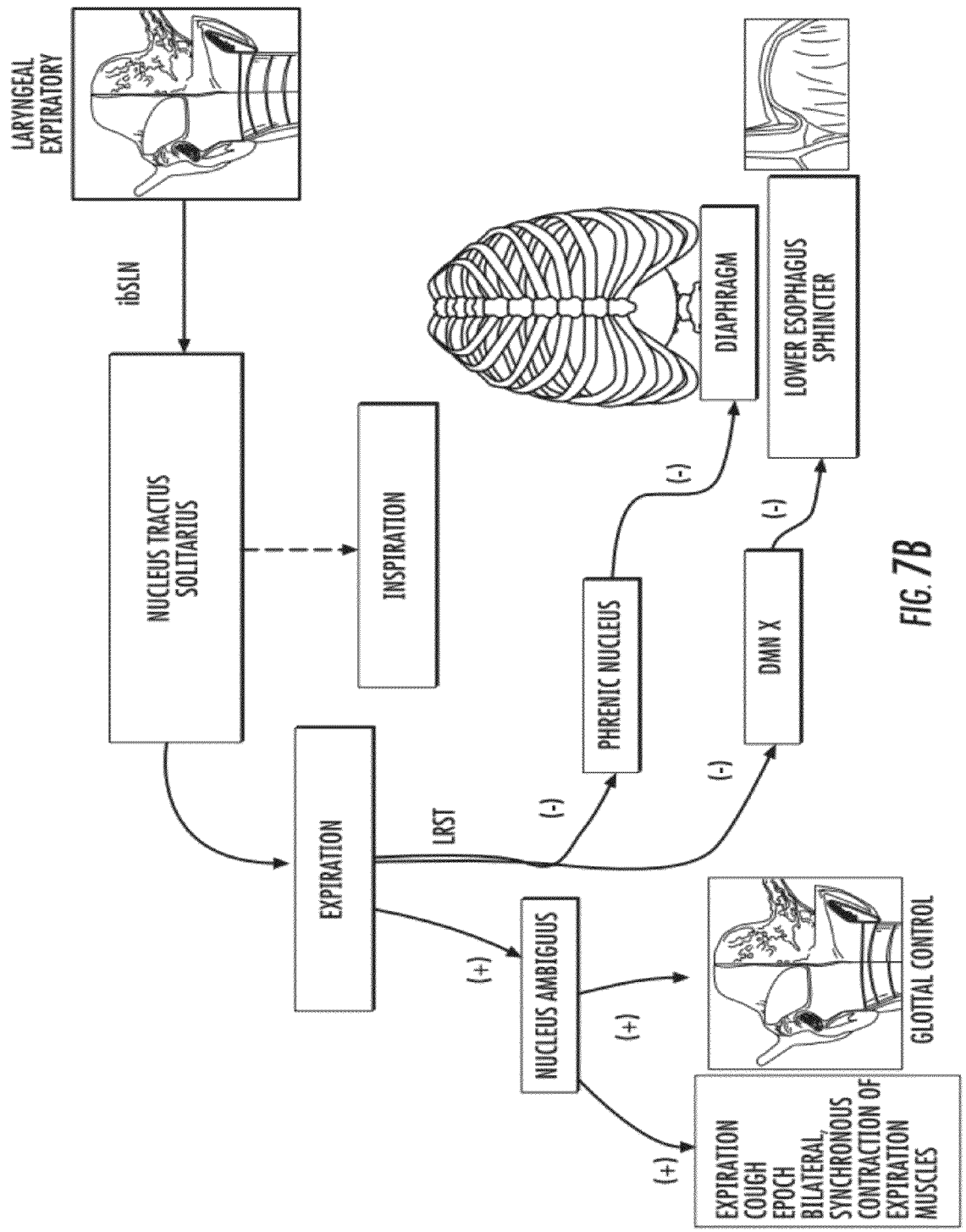
FIG. 7B is a nerve conduction graph showing the laryngeal expiratory reflex.

The laryngeal afferent fibers to the NTS that activate the LER for airway protection or involuntary coughing are shown in FIG. 7B and do not appear to activate the inspiration continence reflex (ICR) and breathing, during the duration of the involuntary LER cough epoch. The laryngeal afferent fibers to the NTS activate the LER for airway protection or involuntary coughing and do not appear to activate the ICR and breathing, during the duration of the involuntary LER cough epoch.

Figure 9:
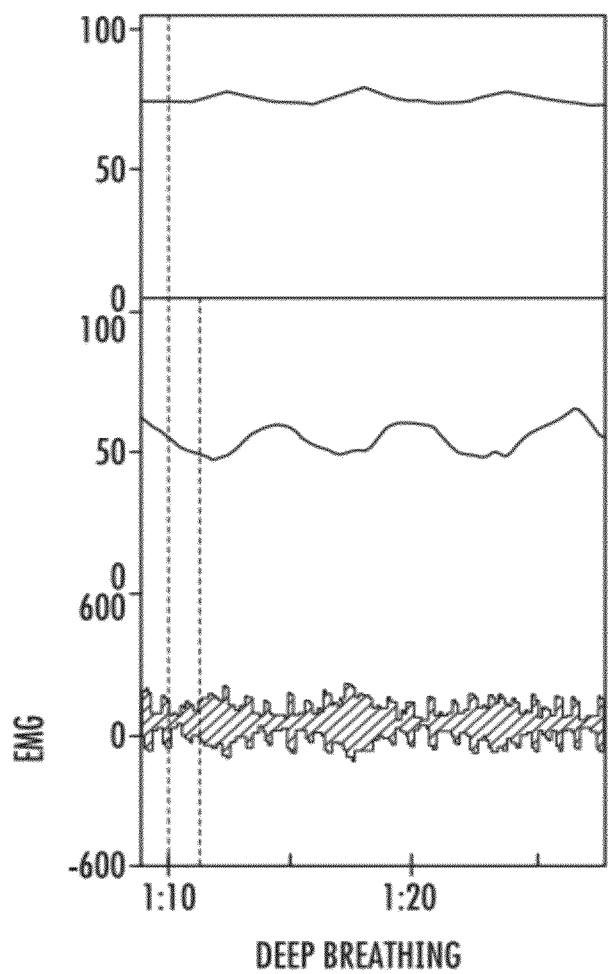
FIG. 9 is a graph showing the relative latencies of the IUS and LES with deep inspiration and expiration.

The unexpected rapid closure and pressure elevation of the IUS within one second as shown in FIG. 9, after the initiation of each inspiration, can be explained by the fast conduction (30-60 m/sec) of the descending pathway in the spinal cord from the nucleus tractus solitarius (NTS) via the lateral reticulospinal tract to the neurons in the sacral autonomic nucleus at S2-4 of the spinal cord. The 25 cm long, unmyelinated, peripheral nerve component conducts at 0.5 m/sec, and takes less than one second to close the IUS. The LES closure was slightly delayed by approximately 1.5 seconds after the initiation of inspiration. This may be due to the different pathway from the NTS to the dorsal motor nucleus of X and a long peripheral, unmyelinated vagal nerve (50 cm) to the LES. Both of these closures (pressure waves) occur before the peak EMG activity, which is before the elevated intra-abdominal pressure (IAP) event in a voluntary respiratory maneuver, e.g., voluntary cough or a Valsalva maneuver.

Figure 10A:
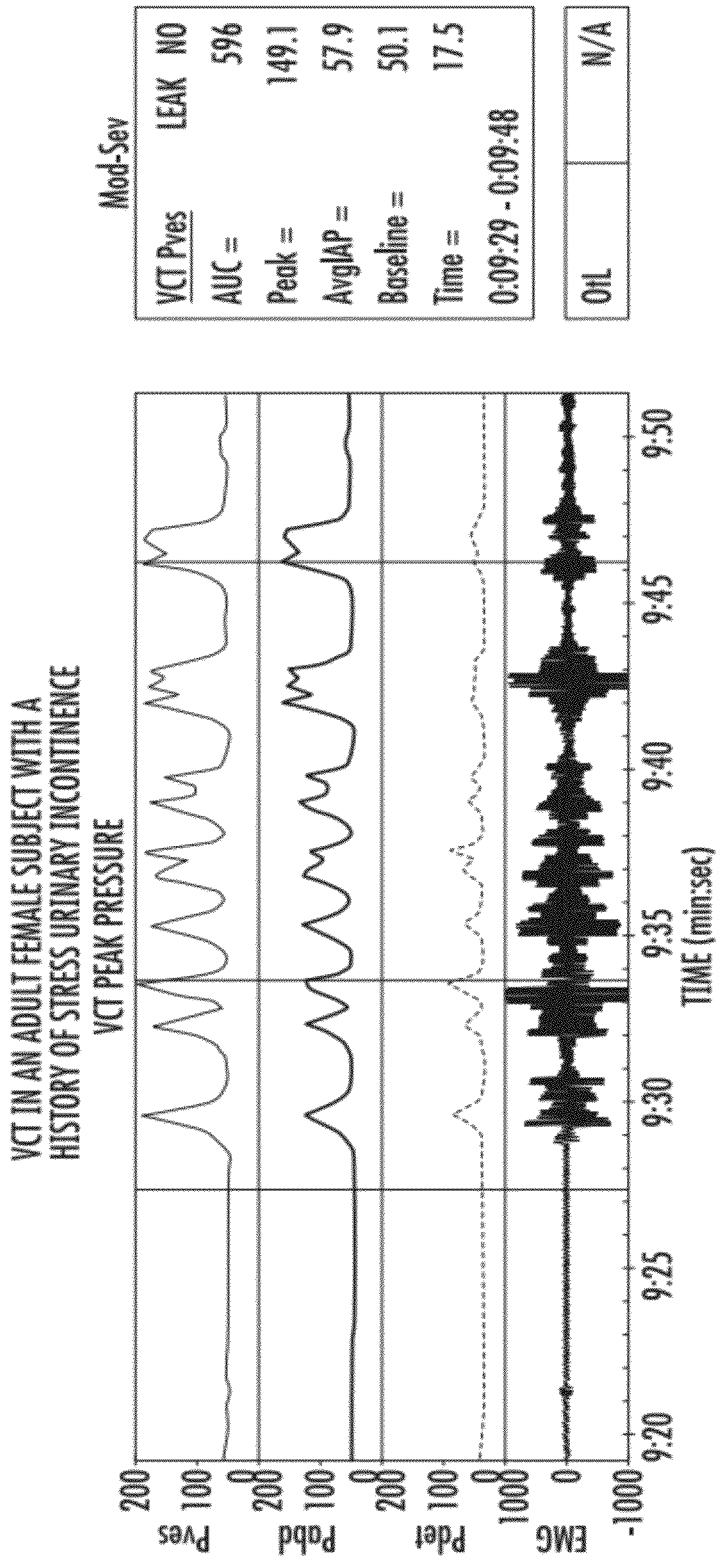
FIGS. 10A and 10B are respective urodynamic (UD) tracings of a series of forcible voluntary cough in a female subject who has moderate/severe SUI followed by the induced reflex cough test.

A urodynamic tracing of a series of forceful VC in a female subject, who has moderate/severe SUI is shown in FIG. 10A. The urinary bladder was filled with approximately 300 ml of saline and intravesical and rectal pressure catheters were used.

Figure 10B:
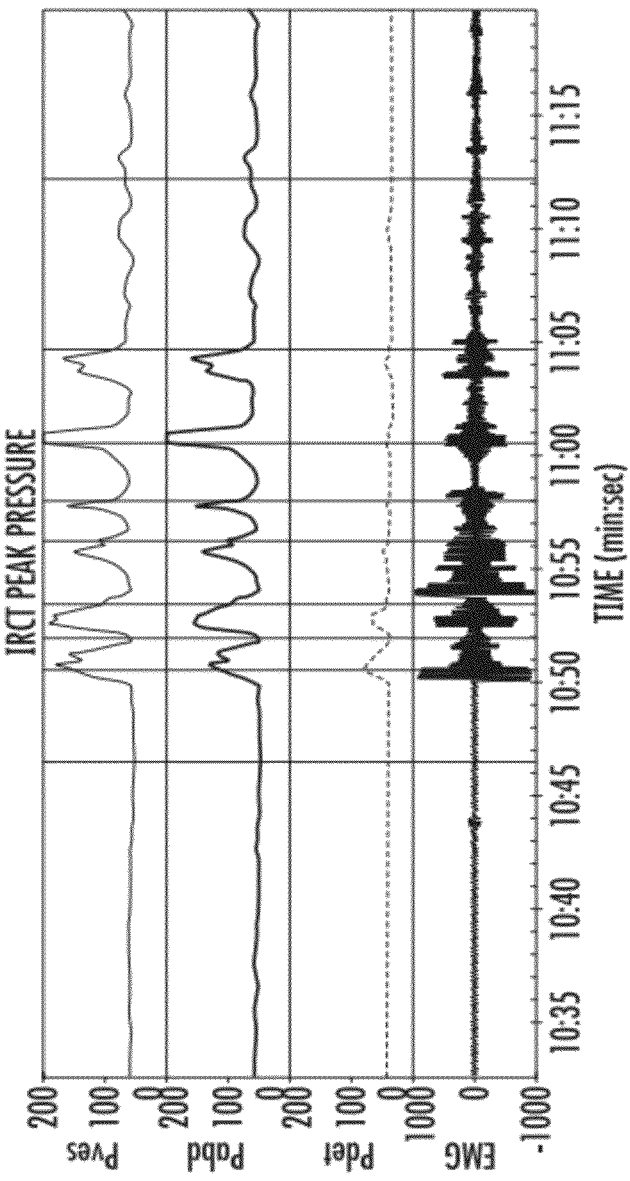
Figure 11:
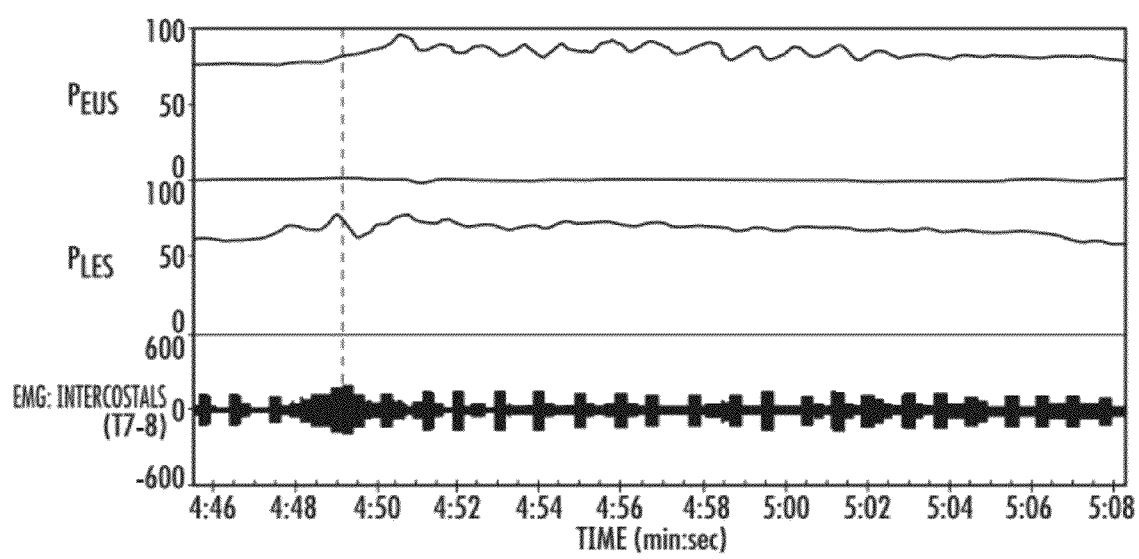
FIG. 11 is a graph showing the results of the breath-hold with the maintained pressure elevation in the LES and IUS.
Figure 12:
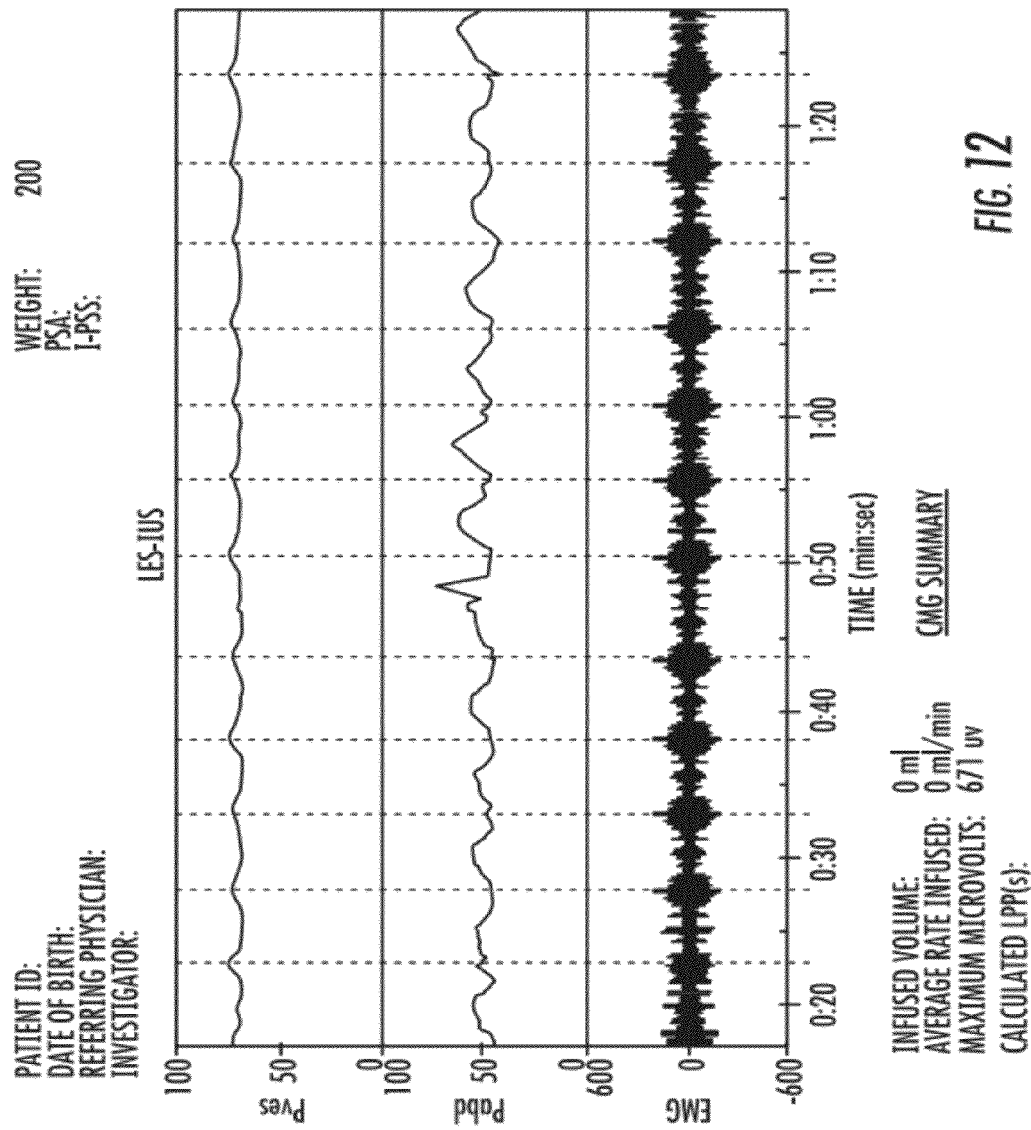
FIGS. 12-16 are EMG and catheter pressure results for the LES-IUS in which dotted vertical lines in FIGS. 12, 13 and 16 indicate the internal urethral sphincter (IUS) synchronously contracted with deep inhalation (inspiration).
Figure 13:
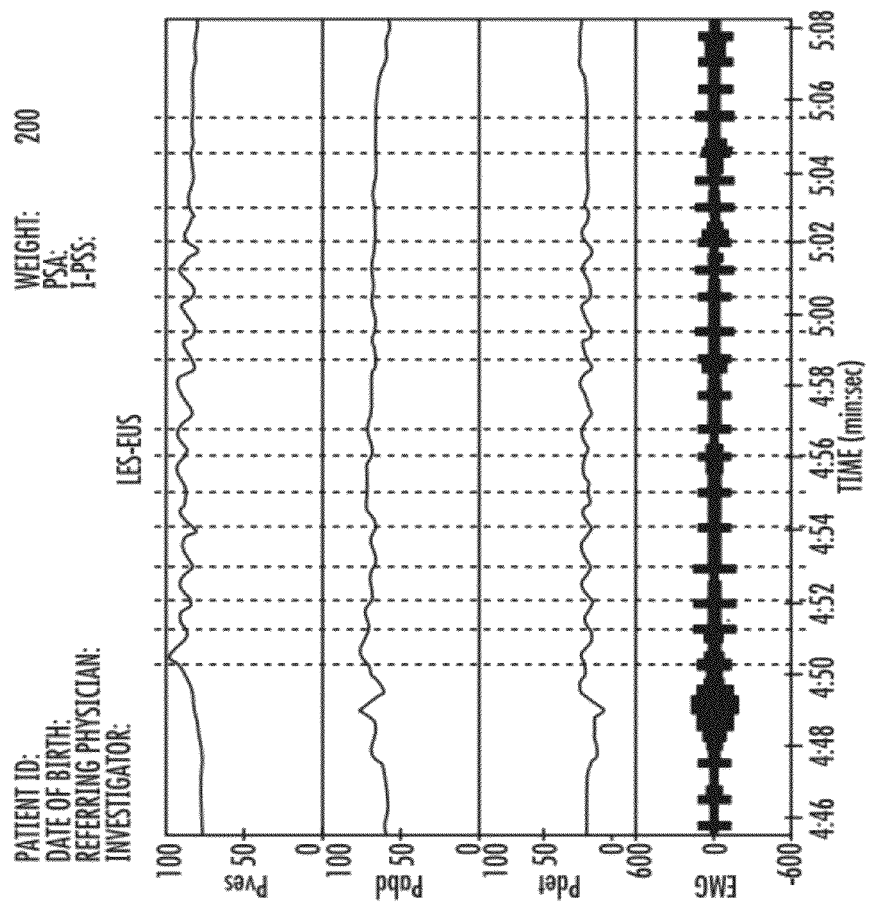
Figure 14:
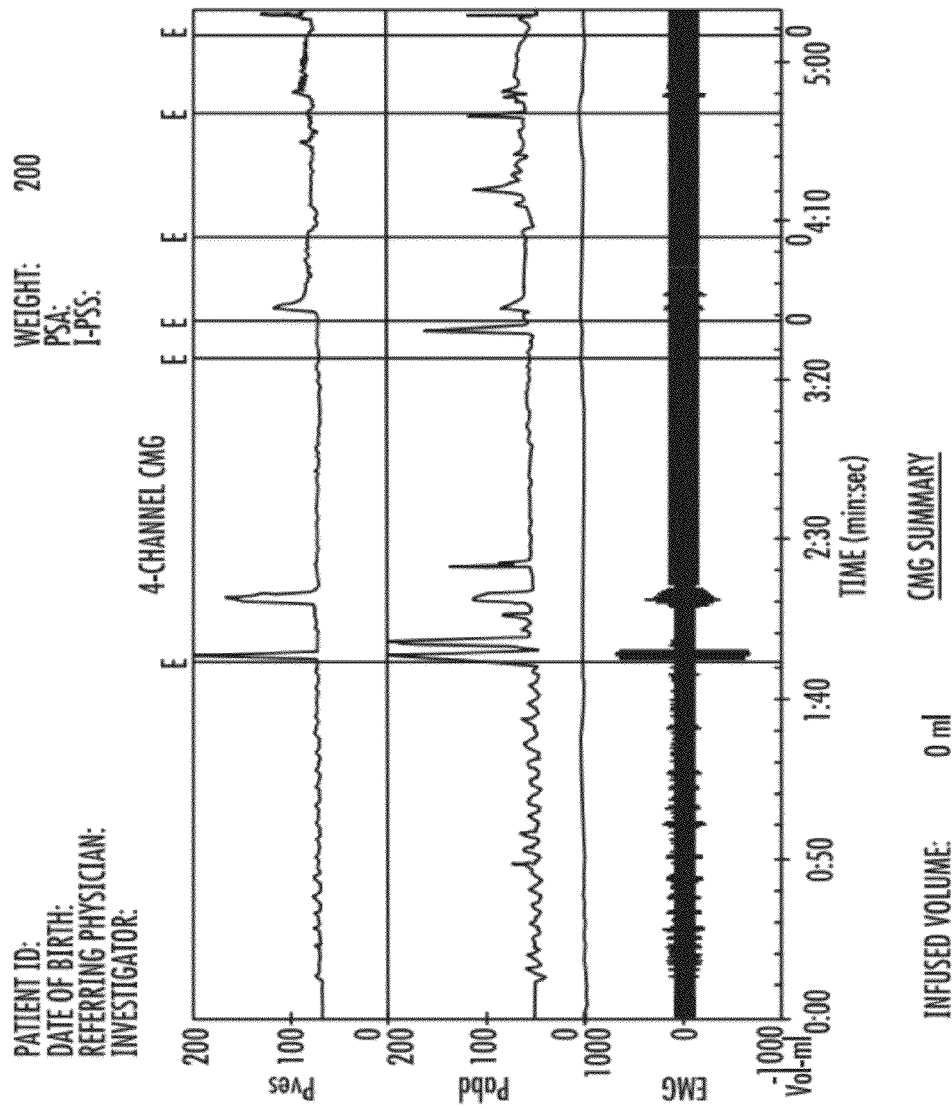
Figure 15:
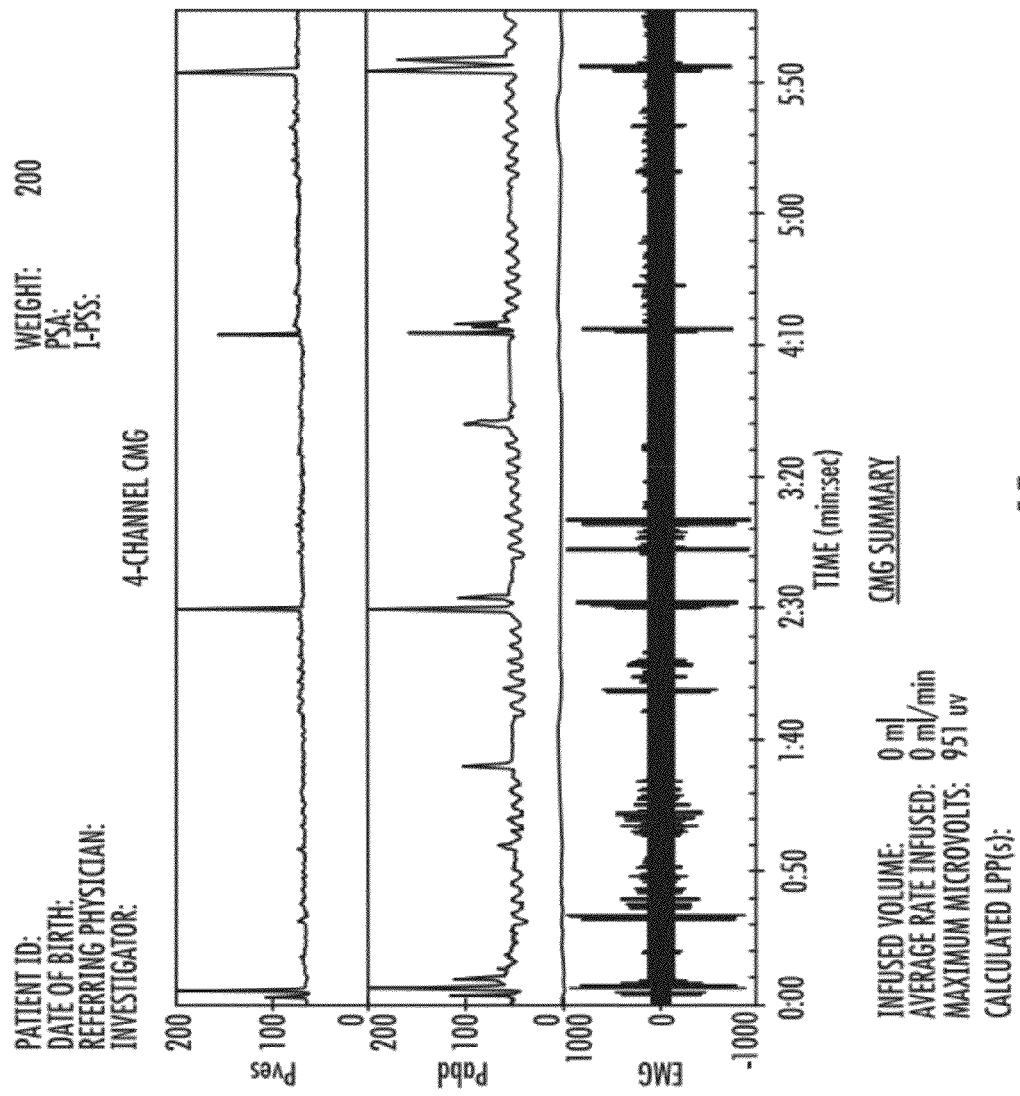
Figure 16:
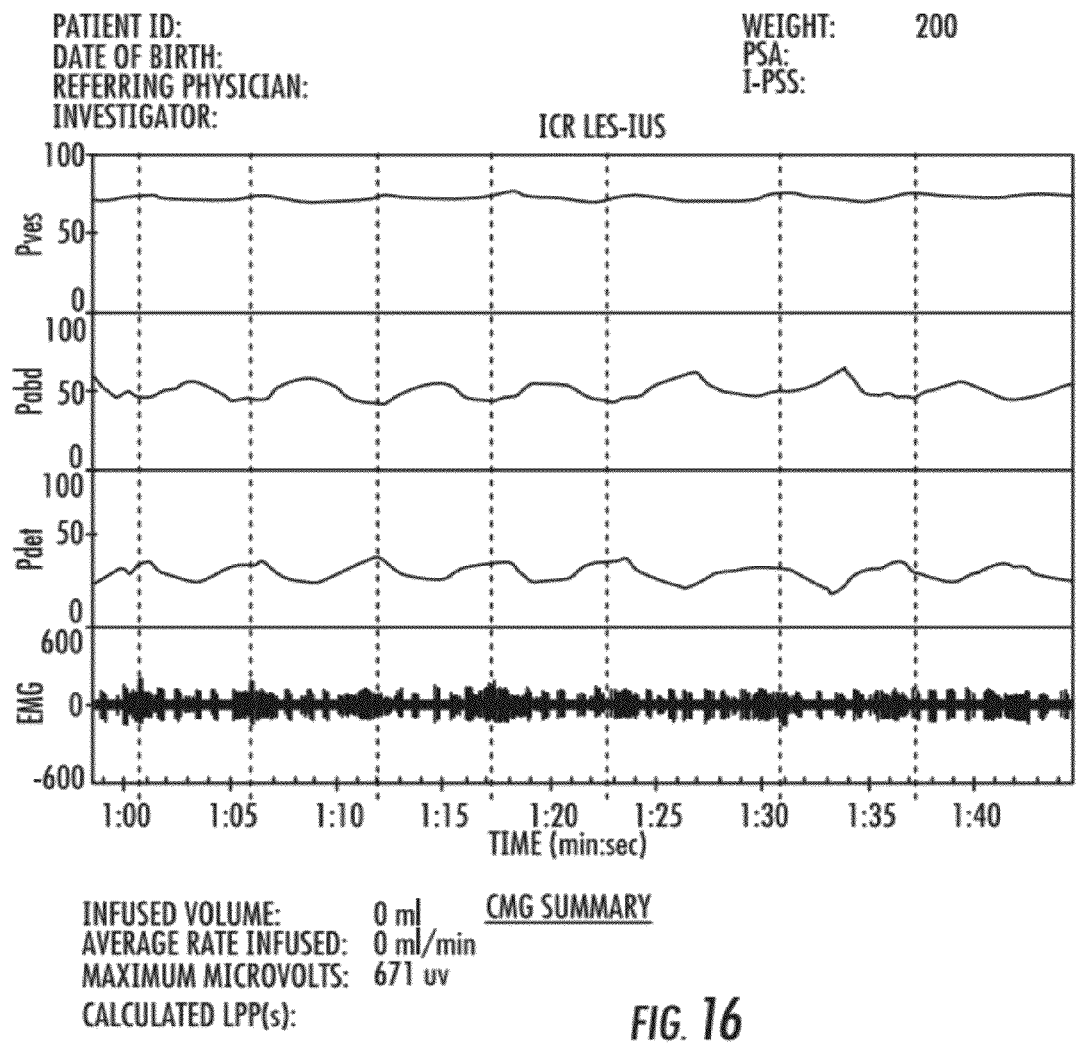

VC did not elicit SUI despite the series of vigorous individual consecutive inhalation VC efforts. The subject showed an almost two-fold increase in average IAP with VC, each cough was preceded by a deep inspiration (inhalation). During VC, the deep inspiration that preceded VC activated the ICR and closed the IUS and resulted in a false negative result for SUI in this "moderate to severe" subject. During the involuntary reflex cough epoch as shown in FIG. 10B, the iRCT UD tracing revealed multiple urinary leaks indicated by the marked vertical lines despite lower average IAP measurements compared to VC breath-hold with maintained pressure elevation in the LES and IUS is shown in FIG. 11 corresponding with overlying voluntary contractions of the external urethral sphincter (EUS) and pelvic floor musculature. During contractions of the EUS and pelvic floor muscles, the tonicity of the LES remained relatively unchanged. Breath-hold with maintained pressure elevation in the LES and IUS corresponded with overlying voluntary contractions of the EUS and pelvic floor musculature. During contractions of the EUS and pelvic floor muscles, the tonicity of the LES remained relatively unchanged.

Breuer's original, classic publication reported the fundamental role of pulmonary inspiration and expiration afferent fibers and established a benchmark for respiratory physiology. Some studies further identified expiratory muscle activation as an extension and component of the Breuer reflex. It appears from a review of the literature that there have been no publications of the role of the Breuer reflex in activation of parasympathetic motor nuclei such as the dorsal motor nucleus of X for the LES or the sacral autonomic nucleus for the IUS until the recent clinical trials and pilot studies as described. These studies suggested the role of respiratory maneuvers that control the closure and pressure of the IUS and LES during inspiration and released with expiration and appeared to be coordinated and synchronized with the rate and depth of inspiration. This can refer to the circuit as the inspiration continence reflex ICR in FIG. 4B.

It has been reported that control of the LES may be due to upper and lower esophageal reflexes and diaphragmatic reflexes, i.e., crural reflex. The literature refers to transient relaxation or inhibition of the LES in association with swallowing, obstructive sleep apnea, mechanical ventilation and a negative pressure body ventilator. In animal and human studies, respiration pressure "artifacts" when using manometry have often been dismissed, ignored, or attempted to electronically filter out respiratory pressure related activity in the LES and IUS.

Animal models that require cannulation for respiration, and/or positive mechanical ventilation or anesthetized and paralyzed animals or humans may have been unobservable or over-looked activation of the ICR. Some references described a "straining crural reflex," during the Valsalva maneuver, which caused LES closure by esophageal-diaphragmatic reflexes. In humans, using a negative pressure body ventilator ("iron lung"), the pulmonary inspiration afferent fiber activity was abolished using negative pressure to inspire for healthy, non-anesthetized subjects. This type of negative inspiration pressure ventilation and the absence of the subject's initiation of pulmonary inspiration afferent fibers abolished or significantly diminished manometric pressure at the LES during inspiration.

Although the pressure changes in FIG. 9 were synchronized with inspiration, the timing differences of the IUS and LES may be due to the different central and peripheral components of the IUS and LES pathways. The IUS consistently activated before the LES pressure wave with slight, but consistent, time delay. The IUS has a rapid conducting central component from the NTS to the sacral autonomic nucleus at $S_{2-4}$ of the spinal cord and a short, unmyelinated peripheral nerve component (inferior hypogastric plexus). The LES has primarily a long, slow conducting, unmyelinated peripheral component via the vagus nerve (esophageal plexus). The IUS appeared to respond only to inspiration and released with expiration. During breath-hold, the elevated pressures of the IUS and LES were sustained, and volitional EUS and pelvic floor musculature contractions were observed on top of the IUS pressure wave, which were not present on the elevated LES pressure tracing as shown in FIG. 11.

These studies with the IUS and LES suggest that if the pulmonary inspiration afferent fibers were naturally activated, the sphincters closed with every inspiration and released with every expiration. When inspiration preceded expiration as in quiet breathing or voluntary maneuvers like the VC, Valsalva maneuver or sneezing these sphincters release with expiration. The degree of sphincter closure appeared to vary with the rate, depth or volitional modification of inspiration, and released with expiration. The LES and IUS pressure responses seen in this study appear similar to the "respiration artifacts" in other studies. It is possible that the IUS closure and presssure elevation related to inspiration could give a structural advantage at the neck of the urinary bladder to prevent incontinence as shown in FIGS. 10A and 10B. It is also possible that pulmonary inspiratory afferent fibers to the nucleus tractus solitarius (NTS) may co-activate both the phrenic nucleus and dorsal motor nucleus of X (DMN). The LES closure and pressure elevation shown in FIG. 6 via the DMN may coincide with simultaneous activation of the diaphragm to prevent hiatal herniation during elevated intra-abdominal pressure events such a Valsalva maneuver or labor.

A limitation of this study is the fewer number of subjects. However, the findings were method dependent and reproduced in the four normal, healthy subjects for BSV and the cohort subject for both the BSV and catheter studies. Further work on both normal subjects and subjects who have pathologically related conditions with morbidity. Understanding the normal physiology of the LES and IUS will lead to improved treatment decisions and outcomes when treating pathological conditions of these structures.

FIGS. 12-16 show EMG and catheter pressure results from a clinical trial. Critical lines include the EMG results, the abdominal pressure and vesicular pressure during the LES-IUS testing. Also shown are the detrusor pressure in FIG. 16 for the CMG summary. The four-channel CMG is displayed.

The dotted vertical red lines indicate that the internal urethral sphincter (IUS) is synchronously contracted with deep inhalation as inspiration. Contraction of the lower esophageal sphincter (LES) was also in phase with inspiration although slightly delayed as a slower response. The latter can be explained by the different neural anatomical and neural physiological pathways that convey these responses. The LES pathway has a slow conducting and much longer in length peripheral pathway as nerves and the path for the IUS is initially conveyed via descending tracks in the brain stem and spinal cord and distribute to the IUS via the relatively shorter peripheral nerves. These peripheral nerve components in both pathways is the slowest conducting component and explains the slight delay contraction of the LES, which was still synchronized with inspiration.

Using an involuntary cough test, specifically for the LER, inhibits or does not activate closure of the smooth muscle sphincters. This has been demonstrated with the LES using barium and scintiegraphy and the IUS with incontinence, compared to voluntary maneuvers. The analysis so far and described concerns barium and not scintiegraphy. Some scintiegraphy tests demonstrate some delayed reflux with the involuntary reflex cough test. Clinical trials using scintiegraphy was not as adequate as using barium because of the delay. With barium, the same approach can be used because when standing, barium goes straight into the stomach during the iRCT because the LES is inhibited. The reverse process occurs if the stomach were full of barium, and the subject placed down 45 degrees to elevate the IAP with the iRCT. If the gastric valve, which is passive, is incompetent, then the LES is inhibited during the 14.8 average seconds of involuntary cough, reflux would be demonstrated and even the severity determined. Using the system and methodology as described, it is possible to inhibit breathing and elevate IAP so the LES is inactivated, leaving the functional closure of the passive gastric valve function isolated.

The laryngeal expiratory reflex (LER) is not influenced by cognition. Dysphagia, hemi-sensory neglect or proprioceptive deficits can be measured. All LER cough muscles are recruited bilaterally and simultaneously. There is a C5 threshold stimulus for LER.

The voluntary cough (VC) is influenced by cognition, dysphagia, hemi-sensory neglect or proprioceptive deficits. The VC muscles depend on cortex and cognition and are recruited by incremental activation. Dysphagia and airway protection separate cranial nerves and must be evaluated separately.

Coughing triggers a coordinated contraction of the thoracic, abdominal and pelvic muscles. The contraction of these muscles causes an increase in intra-abdominal pressure (IAP), which pushes the diaphragm upward thus supplying the force for clearing the airway via coughing. The iRCT can be used in conjunction with an electronic device, such as the handheld processing unit as shown in FIGS. 21 and 22, which measures and analyzes intra-abdominal pressures during coughing and measures and assesses the cough force necessary to clear the upper airway of aspirants. During reflex coughing with this type of test, the increase in IAP makes it essential to close off the bladder and bowel. Otherwise, urinary leakage, i.e., stress urinary incontinence (SUI), will occur. This is useful in diagnosing and accessing treatment effectiveness in this example.

The VC is a cortically mediated, conditioned (learning) response. It is not a reflex. It is a learned or developed neuromuscular sequence, which can be disrupted or absent in some stroke patients. All VC events begin with an inspiration (inhalation), which has a premotor effect on the muscle tone of the abdominal and pelvic sphincters. It can also be (and often is) attenuated by the subject during the UD exam, since they empirically know the 'level' of effort that would produce a leak. After reviewing the literature on micturition, and trying to connect the VC system, cortically mediated micturition and the LER, it became clear that they are not the same circuits and share only some motor nuclei, but probably not the same terminations in these nuclei. VC does not use neurons in the nucleus tractus solitarii (NTS), the principal sensory nucleus that mediates the LER patterned reflex pattern.

The LER has a specific central pattern generator in the medulla that is programmed (wired) to elicit a rapid neural protective reflex. It clears the upper airway of potential aspirants and closes abdominal and pelvic sphincters. This is a symmetrical and synchronous reflex to the associated muscle. The smooth muscle of the internal urethral sphincter, however, is quite slow compared to the striated muscles of the EUS. This histological difference along with urinary bladder structural issues, patient demographics, and the possibility of dyssynchronous firing of the bilateral LER circuits (a useful test in itself) may also be contributing factors. Nevertheless, the iRCT test is a very reliable indicator as to the functional integrity of the CNS component of the LER circuit and the integrity of the external urethral sphincter (EUS). If the EUS fails, SUI (urinary leakage) is almost immediate. If the EUS is intact and functioning correctly, SUI is a very unlikely issue. This scenario relates to the evolution of upright posture, the displacement of the urinary bladder into the pelvis in the late teens, and a social need for volitional control (which we have, except in situations where there is sphincter deficiency and an abrupt onset of intra-abdominal pressure).

The LER patterned reflex circuit is associated with a noxious stimulus (food or fluid aspiration) or a clinical test (such as the iRCT that mimetics the natural effect of a noxious stimulus) that triggers supraglottic receptors (superior to the vocal folds) in the larynx without a preceding inspiration. This last point plays a critical role in the LER circuit and its role in continence. During the LER cough epoch it is not possible to inhale (inspire), which may be due to inhibition or blockade of the phrenic nucleus or an effect on the inspiratory center in the brainstem, or both. Nevertheless, the subject cannot inhale during a properly administered iRCT. Without an inspiration (inhalation), the "presets" for the urethral sphincters appear to be quite different as shown on our clinical trial. The LER circuit involved a restricted region of the NTS and adjacent neuronal clusters. It has extensive reciprocal connections, which interconnect LER circuit neuronal groups with rapid descending pathways in the lateral reticulospinal tract (bulbospinal tract) and lateral vestibulospinal tract. These tracts have strong influences on autonomic nuclei in the spinal cord and motor nuclei to axial musculature.

The LER circuit involves a viscerotopic, restricted region of the NTS and the LER central pattern generator (LER-CPG). LER-CPG has extensive reciprocal connections, which interconnect LER circuit neuronal groups with rapid descending pathways, the lateral reticulospinal tract (bulbospinal tract) and lateral vestibulospinal tract. Strong descending influences on autonomic nuclei in the spinal cord and motor nuclei to axial musculature.

There now follows a description of various catheters and Ng/Og devices that can be used in accordance with a non-limiting example. It should be understood that the different catheters and Ng/Og devices include those with and without esophageal cuffs as described in the various copending applications identified above and can be used in accordance with non-limiting examples. For example, these catheters and Ng/Og devices are shown at FIGS. 3, 31, 32, 33, 51A-51E, 52A-52G, and 53A of the incorporated by reference '281 application that published as U.S. Patent Publication No. 2011/0046653. It should also be understood that some of the Ng/Og tubes as described in these copending applications have lumens for introducing a chemo-irritant for inducing the involuntary reflex cough epoch such that a nebulizer may not have to be used. These Ng/Og tubes can include various lumens for suction and esophageal cuffs. They can include a Salem sump port and an inflation lumen and various radio-opaque markings to aid in device placement. Various pressuring pH sensors can be located along the tube. Further details of such a tube that can be used and modified in accordance with a non-limiting example is set forth in the incorporated by reference '653 patent publication corresponding to application Ser. No. 12/878,281.

Figure 17:
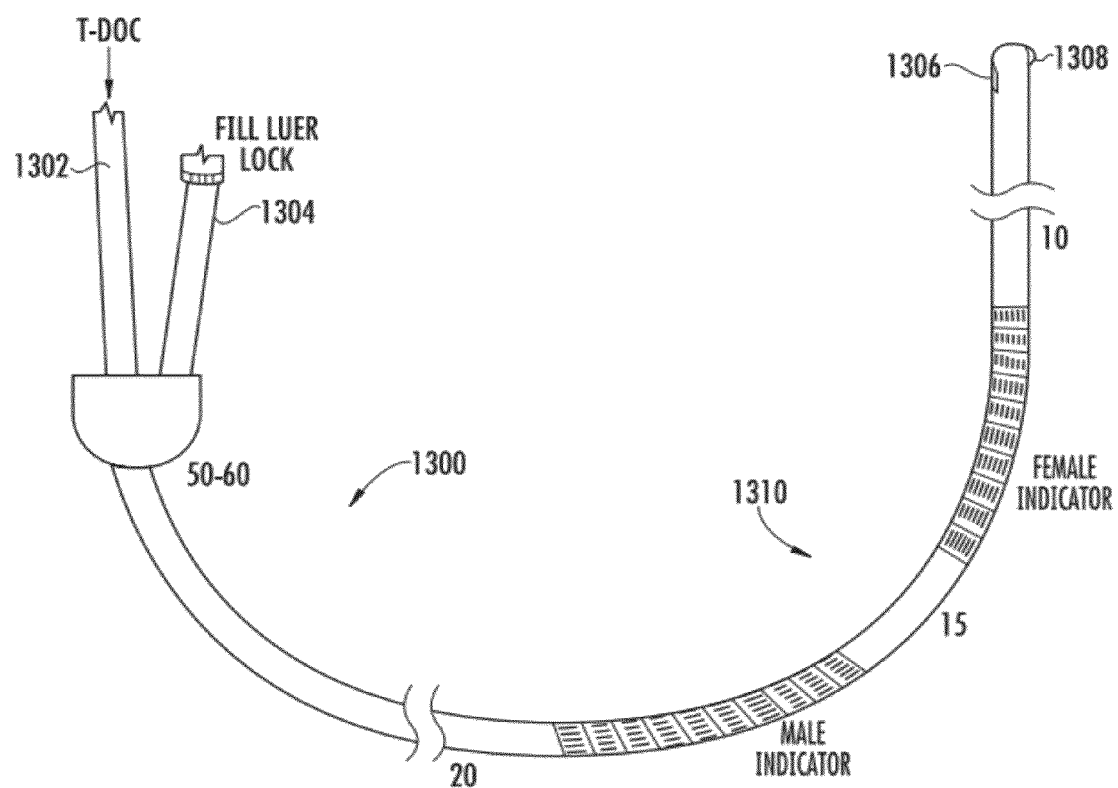
FIG. 17 is a simplified plan view of a catheter that can be used for urodynamic and medical diagnostic testing in accordance with a non-limiting example.

FIG. 17 is an example catheter 1300 that can be used in accordance with a non-limiting example. It is a urodynamic dual lumen catheter formed from a catheter body as an elongated tube with proximal and distal ends and preferably has a smallest external diameter that can contain two lumens within it. It is typically approximately 50 to about 60 centimeters in length. A first lumen 1302 can be used for monitoring bladder activity. In one non-limiting example, it contains a stylet/wire sensor that can be left within the lumen or used alone. A second lumen 1304 permits the filling port to instill fluid into the urinary bladder. The second lumen output is shown at 1306 and a sensor 1308 is positioned at the distal end such as for pressure measurement. This catheter includes a Luer lock end for rapid connection to infusion tubing or a syringe, and can accommodate rates of infusion up to 1,200 ml/hr via gravity flow or 15 ml/sec via manual installation.

The external surface of the catheter has a surface area that contains areas of indicators along its length shown generally at 1310 that operate as a urine leak detect device. These indicators 1310 change color when exposed to two components in combination in accordance with a non-limiting example. This color change can occur with a temperature about 30 degrees Celsius and the presence of urea in a non-limiting example.

The catheter 1300 can be used to evaluate bladder pressures at rest, empty, or with urine, filling with fluid during voiding. Pressure sensors can be located where the internal and/or external urethral sphincters are located. It is used to evaluate for urinary incontinence by detecting a minimal amount of urine loss during voluntary and involuntary maneuvers of the type as described before. The stylet sensor in one non-limiting example is used alone for pressure monitoring while presenting the least amount of disruption/distortion of the urethra and urinary sphincters. The stylet in another non-limiting example is packaged separately and inserted into an existing Foley catheter to measure pressure and function in one non-limiting example.

In one non-limiting example, the catheter is a dual lumen six French catheter of about 50 centimeters and includes the sensor 1308 and fill port at the second lumen 1304. It is inserted in a non-limiting example about 10 centimeters for a female bladder and 15 centimeters for a male bladder. The location of color change indicators 1310 for a female could be about 11-14 centimeters, and for a male, about 16-19 centimeters. In one non-limiting example, the urine pH range is about 4.6 to about 8.

It should be understood that the catheter is preferably a smaller diameter catheter and includes those catheters of 3 (three) and 4 (four) French. The smallest catheter possible is used as a urethral catheter and somewhat smaller than a standard ten (10) French catheter. It has been found that some patients have a tendency to leak with the larger catheter in place because of the size of the catheter or they become obstructed with that catheter in place. Smaller urinary bladder catheters are typically about 6 (six) French and used for neonatal infants. There are some PICC catheters (Peripherally Inserted Central Catheters) that are three (3) and four (4) French. These smaller catheters should be double lumen in this example. This system is not limited in size, but the smaller is advantageous.

The catheter, in accordance with a non-limiting example as described, can have a first lumen 1302 for a sensor probe 1308 and a second lumen 1304 for the filling with liquid. The sensor probe in one example is a "T-doc" as used with an air-charged catheter for pressure sensing and air-charged pressure recording in one non-limiting example. It should be understood that this catheter can be used with or without filling the bladder, and advantageously used in urodynamic testing. The doctor, nurse or clinician does not have to personally bend down and view the urethra area to determine if there is leakage, which is an advantage in a clinical test. Different types of indicators 1310 as chemical indicators can be used.

Figure 18:
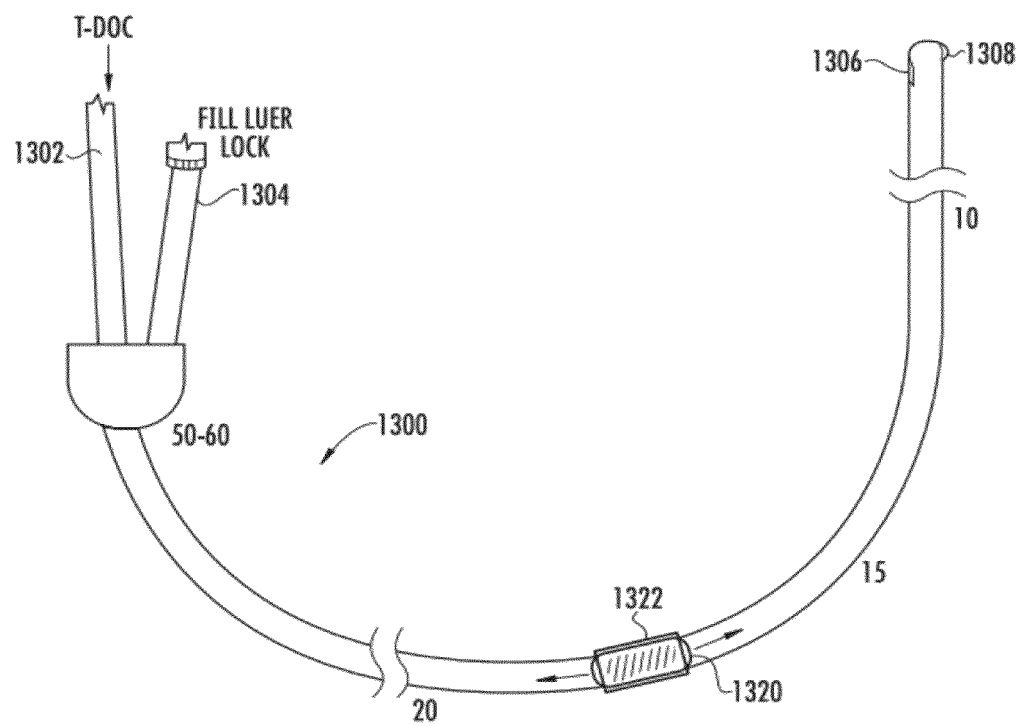
FIG. 18 is a simplified plan view of another example of a catheter similar to that shown in FIG. 17 that can be used for urodynamic and medical diagnostic testing in accordance with a non-limiting example.

In another non-limiting example such as shown in FIG. 18, the catheter includes a support ring 1320 such as a silastic ring that holds a urine-indicating pad or other enzymatic pad 1322 and is affixed to the catheter as a single unit wherein the catheter that measures the intravascular pressure. The silastic ring 1320 carries a color changing pad in this example instead of using color indicators 1310 positioned along the catheter surface as in the example of FIG. 17. This also provides for a urinary leakage indicator. The support ring 1320 slides on the catheter in one example. It is permanently affixed to the catheter, but adjustable in this example. A moisture indicating dye is used in an example on the pad 1322 positioned on the ring 1320. An example of a dye is disclosed in U.S. Pat. No. 4,327,731 as a moisture indicator, and in one aspect could be an enzyme catalyst.

Different types of pads or substrates could be used in combination with the support ring 1320 and moveable along the catheter. This combination catheter and the urine indicating sensor, in one example, are specific for use to determine an instance of stress urinary incontinence. It is possible, however, to add a balloon to this catheter similar to a Foley catheter such that the catheter remains in place. Two catheters are thus possible. For example, a specific catheter and urine indicator are used for stress urinary incontinence. It is also possible to add a balloon with the larger 14, 16, 18 or 20 French catheters as a larger size. A sensing system is included in this example. Added to this catheter is a channel for urine drainage, the sensor, and an indwelling balloon to keep it in place. The catheter, in one example, is used to determine whether the patient can protect their airway in conjunction with the involuntary reflex cough test (iRCT).

The cloth or pad 1322 is attached to the support ring 1320 and includes on the pad a regent that can be permanently attached. It can be a single use catheter for stress urinary incontinence (SUI) testing. It can be included within a test kit and includes the nebulizer (and the drug) for involuntary reflex cough testing as described before.

In one example, it is possible to have a catheter of about three (3), four (4), or five (5) or somewhat larger French that thread inside a regular Foley catheter with pressure measurement capability. The catheter that goes inside the urethra, such as a seven (7) French catheter, can go inside a Foley catheter. In one example, the balloon is part of the smaller catheter and measures or tests for airway protection in the technique as described before.

An enzymatic moisture detector can be used. Initially, any indicators or pad and ring could be covered before catheter use. When needed, the catheter is uncovered and moved into the proper position against the meatus. A first catheter is used with stress urinary incontinence and testing. Another catheter as a second or larger diameter catheter is balloon specific for reflex cough testing to measure intra-abdominal pressure in determination of airway protection.

In an example, temperature is used with the sensor and changes the sensor as an indicator. It is possible to use the presence of urea for sensing urine. One problem is in bladder testing. The bladder is often filled with saline water or other fluid that is not urine. If the indicator is specific to ammonia or urea, then it would not indicate adequately. Temperature is one advantageous solution and a material that is sensitive to temperature change of about 90 degrees is adequate. The fluid is inserted into the bladder and becomes warmer than room temperature. If there is leakage, it changes the color of the catheter even without the presence of urea.

The tip of the catheter can be placed into the urethra and the outside of the catheter includes the indicator. It changes color if there is leakage whether there is urine inside the bladder or just fill. It could change the color of liquid after it leaks. This could be an assurance against false positives such as would occur with perspiration from the doctor's or nurse's hands. If there is a second testing such as in surgery (and the patient hopefully fixed), a different color could be used. In SUI testing, the liquid is placed in the bladder in one example, but would come out a different color when it reacts with the sensor on the bladder near the meatus. This assures that one is viewing a leakage and not a false positive.

There is a possibility for measuring airway using the port in combination. The catheter can be small enough to go into a side port of a Foley catheter similar to a guide wire. Thus it is possible to take the catheter out if it is obstructing in some way and leave a guide wire. It is possible to remove the catheter and still have a guide wire or small catheter that has a sensor probe on the end. Instead of having a dual channel and having a tube inside a tube where one could do a fill around, it is possible to remove the outside tube that is blocking the urethra. It should be understood that the catheter (depending on size and pathophysiology of a patient) can either block the urethra or hold the urethra open, causing additional leakage. Specific catheter designs as described alleviate these problems. With the larger catheters, the larger catheter size is used to fill and is taken out. The inside tube (catheter) stays. A smaller four (4) French catheter has a dual channel, one for the pressure sensor and the other to fill 1200 millimeters an hour and is adequate to cover different possibilities.

Figure 19:
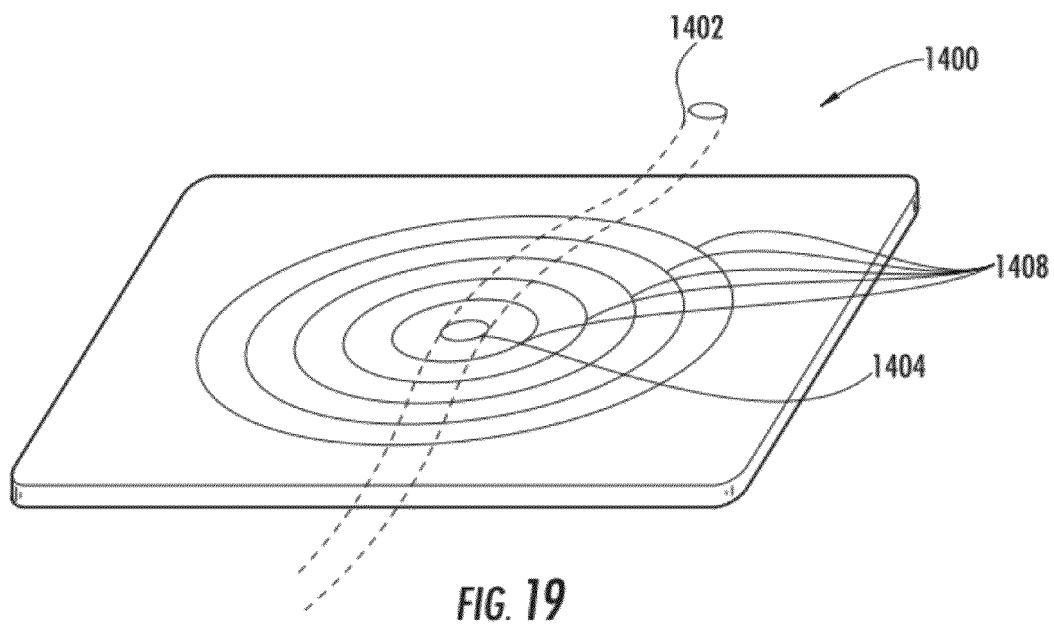
FIG. 19 shows a urinary continence pad that can be used with urodynamic catheters of FIGS. 17 and 18.

FIG. 19 shows an embodiment of a color changing urinary pad 1404 that can be used with a catheter such as described before. The color changing urinary incontinence pad 1400 is used in conjunction with a catheter 1402 and has a small relief cut-out (hole) 1404 in the middle of the pad where the catheter enters. The pad is placed against the underside near the urethra of a female typically and the catheter enters the urethra and extends through the hole in the center of the urinary incontinence pad for fluid flow and testing purposes. The pad could be taped to the underside in the crotch area. For example, when the involuntary reflex cough test is given and the catheter is inserted through the urethra, the patient is prone to leak urine in some examples. This pad includes concentric rings 1408 around the center catheter cut-out at preferred 10 millimeter intervals for a target area of 50 millimeters. In one non-limiting example, a nitrogen-ammonia (NH3) region is used to identify positively the presence of urine on the pad. The target intervals of 10 millimeters each are used to determine how much leakage and incontinence occurs during, for example, a reflex or involuntary cough test as described before. The different concentric areas have different amounts of reagent in a non-limiting example or different reagents to allow different color changes at the spaced intervals depending on the amount of urine leakage.

The various Ng/Og devices as disclosed in the '257, '281 and '316 applications and published as the respective '157, '653 and '211 publications that are incorporated by reference disclose various Ng/Og devices that could be used or modified for use with the system and method in accordance with a non-limiting example.

As noted in these published applications, the esophagus enters the stomach at the cardial orifice to the left of the midline at the level of the 7th left costal cartilage and T11 vertebra. The abdominal part of the esophagus extends from the esophageal hiatusis in the right crus of the diaphragm to the cardial (cardiac) orifice of the stomach. This area is only about 1.25 cm long.

Food passes through the esophagus rapidly because of the peristaltic action and is typically not dependent on gravity. The esophagus is attached to the margins of the esophageal hiatus in the diaphragm by the phrenicoesophageal ligament, an extension of the inferior diaphragmatic fascia. This ligament permits independent movement of the diaphragm and esophagus during respiration and swallowing. The esophagogastric junction lies to the left of the T11 vertebra on the horizontal plane that passes through the tip of the xiphoid process. Immediately superior to the esophagogastric junction, the diaphragmatic musculature forming the esophageal hiatus functions as a physiological inferior (lower) esophageal sphincter (LES) that contracts and relaxes. The sphincter mechanism for the LES is typically efficient in preventing reflux of gastric contents into the esophagus based on radiological studies. The lumen of the esophagus is normally collapsed superior to this level to prevent food or stomach juices from regurgitating into the esophagus when an individual is not eating.

Barium fluoroscopic studies of the esophagus normally show three constrictions of the esophageal lumen due to impressions from adjacent structures. These are possible locations for placing a device for reflux analysis and GERD treatment.

A first constriction is the cervical constriction (upper esophageal sphincter). The superior aspect of the esophagus is the pharyngoesophageal junction, and is approximately 15 cm from the incisor teeth. The cricopharyngeus muscle creates this cervical constriction, which is located at approximately the level of the sixth cervical vertebra.

A second constriction is the thoracic (broncho-aortic) constriction. The arch of the aorta and the left main bronchus cross the esophagus and create esophageal constrictions as seen on anteroposterior and lateral views, respectively. The constriction caused by the arch of the aorta is 22.5 cm from the incisor teeth and the constriction formed by the left main bronchus is 27.5 cm from the incisor teeth.

A third constriction is the diaphragmatic constriction. The esophageal hiatus of the diaphragm is approximately 40 cm from the incisor teeth and forms the diaphragmatic constriction. This is at the level of the lower esophageal sphincter. Pressure sensors are often placed at this location.

The presence of these constrictions is important when placing the device such as described with an esophageal cuff, which would help prevent the reflux of gastric contents into the upper esophagus and pharynx. The placement of the device in one example is suggested inferior to the bronchoaortic constriction (27.5 cm from the incisor teeth), but superior to the diaphragmatic constriction at 40 cm from the incisor teeth. The device typically should not be placed in regions of the esophagus with pathological involvement of the esophagus. For example, the device could be positioned mid-esophagus at about 2 to about 3 cm below the aortic notch and that has been found to be a preferred position in some examples.

Figure 20:
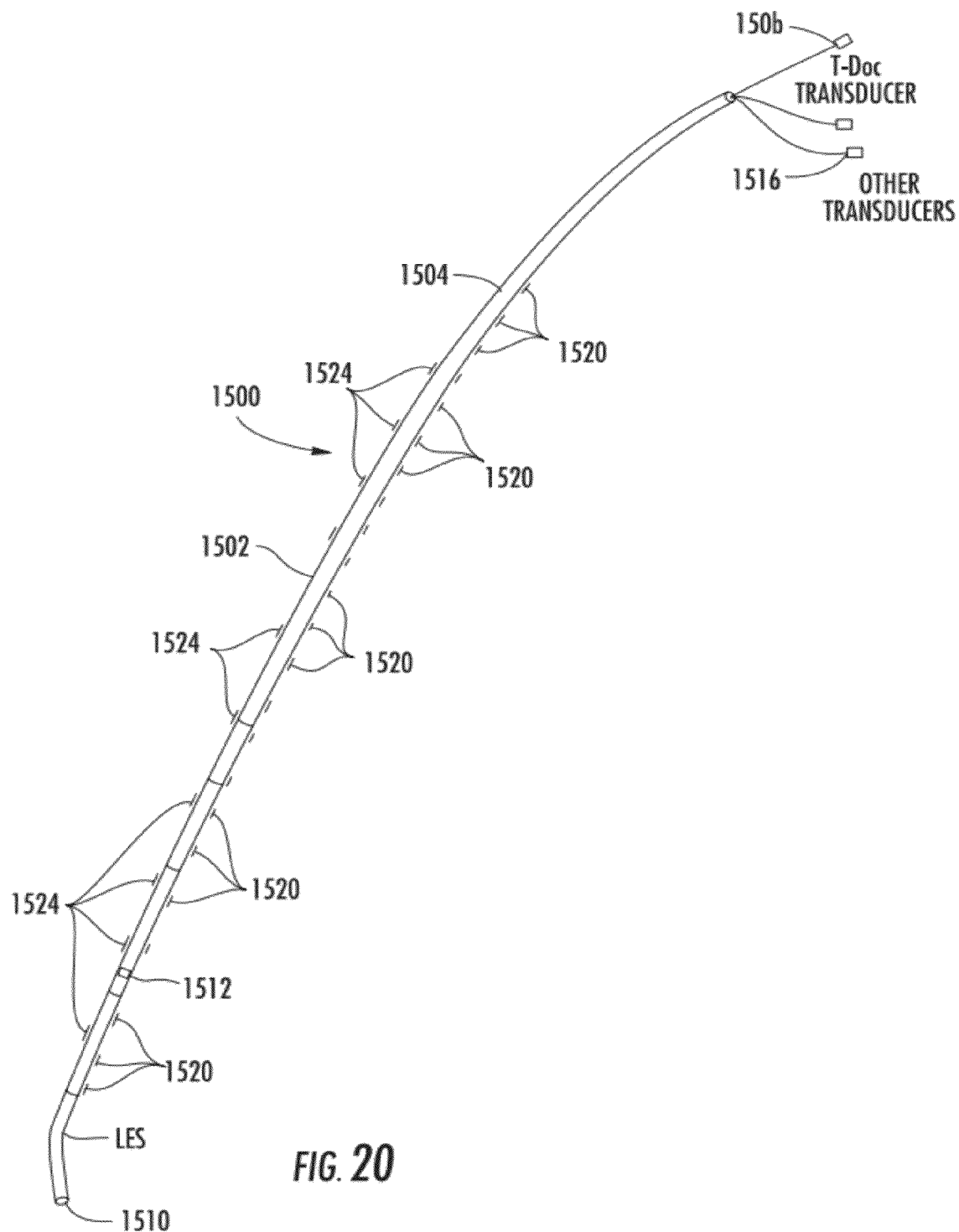
FIG. 20 is a plan view of an Ng/Og device or catheter that can be used for testing for acid reflux.

FIG. 20 shows a catheter 1500 as a device used in a method for diagnosing reflux during an involuntary event such as the involuntary reflex cough test such as disclosed in copending patent application Ser. No. 13/354,100 filed Jan. 19, 2012, and the '257, '281 and '316 applications. As illustrated, this catheter 1500 does not include any cuff as in previous embodiments shown in FIGS. 6A-6E and 7A-7G and includes a catheter body 1502 having a single lumen 1504 in this example with a T-DOC transducer 1506. It is formed as a small, semi-soft catheter. The adult size is about 6 French and the pediatric size is about 1-2 French. Two pressure sensor areas 1510, 1512 are formed for sensing pressure, for example, by using pressure transducers that are placed at the tip of the catheter and approximately 10-15 centimeters from the tip. Different types of sensors could be used and transducer leads 1516 could extend along the side or in the catheter to the end. The catheter could be an air charged catheter. In one example, the catheter is coated with a pH sensitive material 1520 that will change color when exposed to a pH less than about 4.0, indicating reflux. Measurement markings 1522 can be inserted or printed throughout the length of the catheter. In one example, the catheter is an air-charged (T-DOC) for pressure measurement, but other types of sensing mechanisms such as pressure sensors could be used as understood by those skilled in the art. Fiber optics could be used. The catheter is radio-opaque and includes such markings 1524, if radiologic placement is required and it can include in-patient and out-patient indications.

The catheter can operate as an Ng/Og device and is inserted orally or nasally into the esophagus and through the lower esophageal sphincter (LES) into the proximal stomach. Placement is measured from the lips (oral) or nares (nasal) to the TMJ (temporomandibular joint) to about four-finger breadths sub-xyphoid for adults.

The first sensor 1510 is located in the proximal stomach and can measure intra-gastric/intra-abdominal pressure. The second sensor 1512 is located approximately in the mid-to-lower esophagus and can measure intrathoracic pressure. A pressure grading can be over the LES. EMG information typically can be measured to simultaneously record changes in pressure and gradients. EMG can be measured from the paraspinals as described before. EMG sensors could be located at selected locations on the catheter for EMG measurement in some examples. The catheter can include color change indicia for the pH sensitive material to measure the height of refluxed, acidic gastric contents. The catheter includes pH sensors as noted before.

The catheter 1500 has the potential to identify SUI in conjunction with bladder catheters, assess neurological airway protection (represented as one summated value) and SUI, and additionally assess bladder physiology and categorize any classification with a programmed algorithm in incontinent patients using this one small catheter with EMG measurement. Any inputs of different values can be to the handheld device as described.

Figure 21:
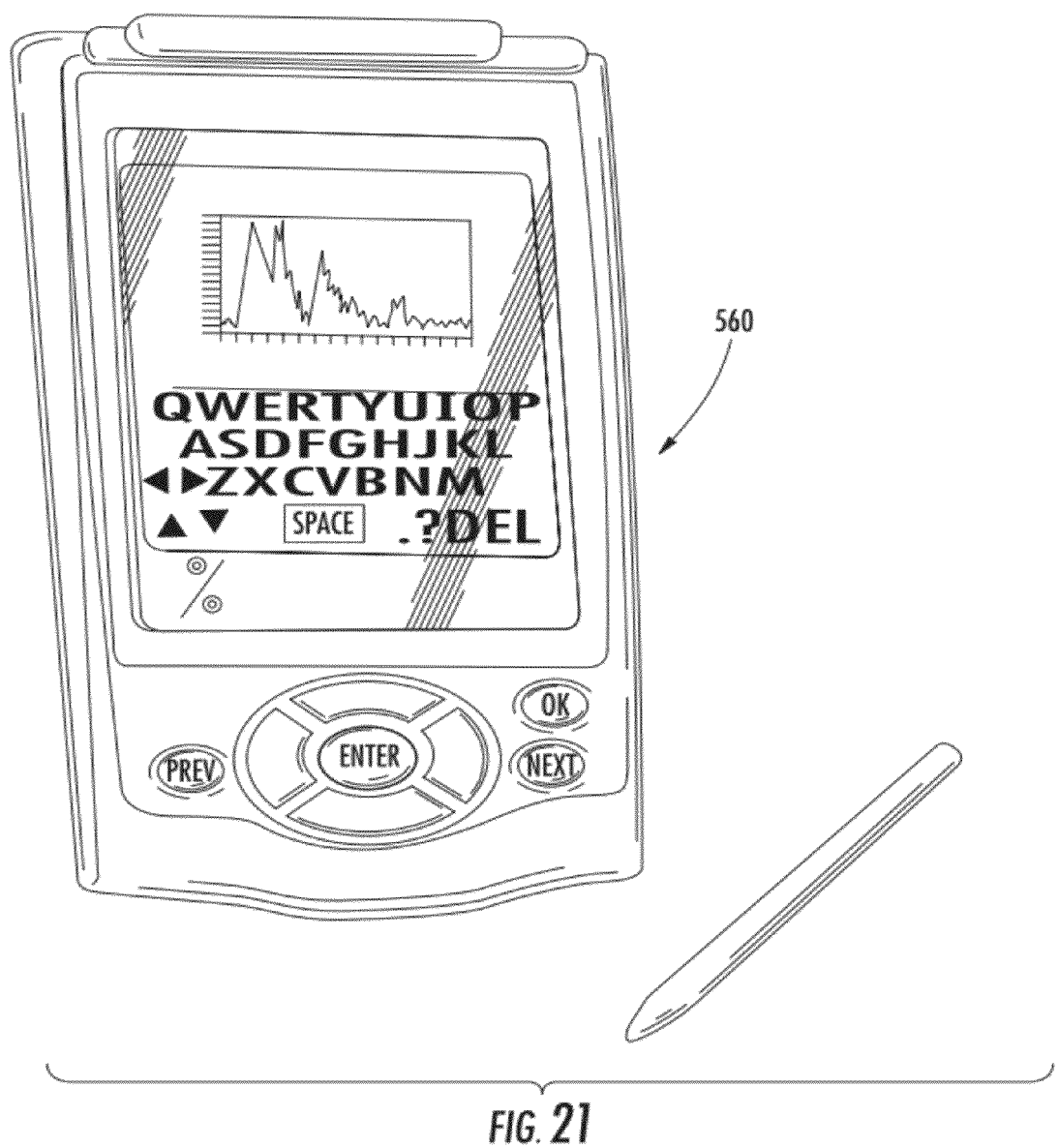
FIG. 21 is a fragmentary plan view of a handheld processing device that can be used in conjunction with various catheters and Ng/Og devices or other catheters and/or nebulizers.

FIG. 21 is an illustration of an exemplary handheld processing device 560 such as described in the incorporated by reference patent applications. More particularly, it should be understood that this handheld processing device 560 can be used by a nurse practitioner or doctor and receive input as wireless signals or as wired input directly from catheters as Ng/Og devices. Also, this handheld processing device 560 can incorporate the circuit and functions as disclosed in the incorporated by reference applications.

Figure 22:
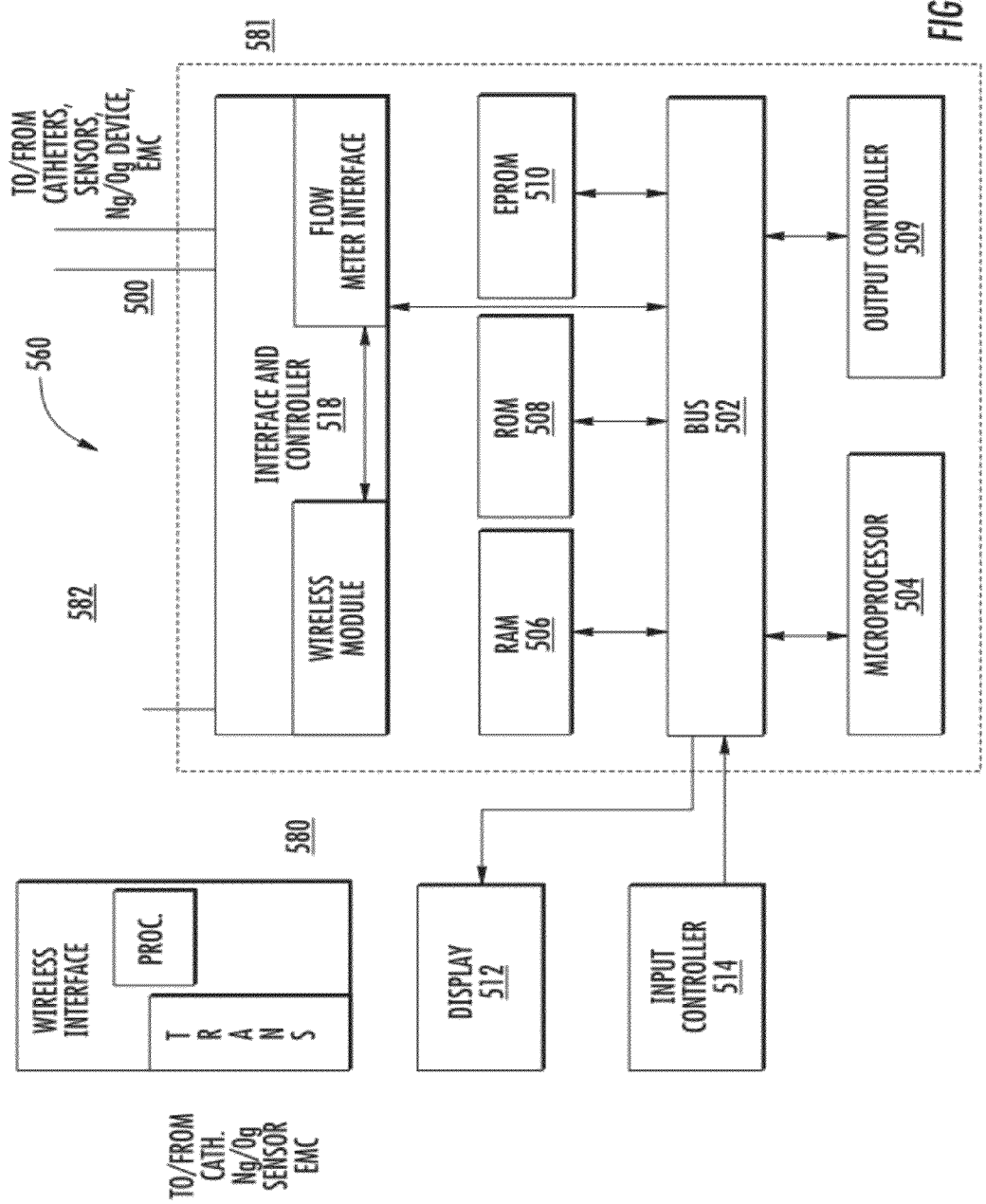
FIG. 22 is a block diagram showing example components of a handheld processing device such as shown in FIG. 21.

FIG. 22 is a block diagram that illustrates a computer system 500 for the handheld processing device 560. Computer system 500 includes a bus 502 or other communication mechanism for communicating information, and a processor 504 coupled with bus 502 for processing information. Computer system 500 also includes a main memory 506, such as a random access memory (RAM) or other dynamic storage device, coupled to bus 502 for storing information and instructions to be executed by processor 504. Main memory 506 also may be used for storing temporary variables or other intermediate information during execution of instructions to be executed by processor 504. Computer system 500 further includes a read only memory (ROM) 508 or other static storage device coupled to bus 502 for storing static information and instructions for processor 504.

Computer system 500 may be coupled via bus 502 to a display 512, such as a LCD, or TFT matrix, for displaying information to a computer user. An input device 514, for example buttons and/or keyboard, is coupled to bus 502 for communicating information and command selections to processor 504. Another type of user input device is cursor control, such as a mouse, a trackball, or cursor direction keys for communicating direction information and command selections to processor 504 and for controlling cursor movement on display 512. This input device typically has two degrees of freedom in two axes, a first axis (e.g., x) and a second axis (e.g., y), that allows the device to specify positions in a plane.

Figure 23:
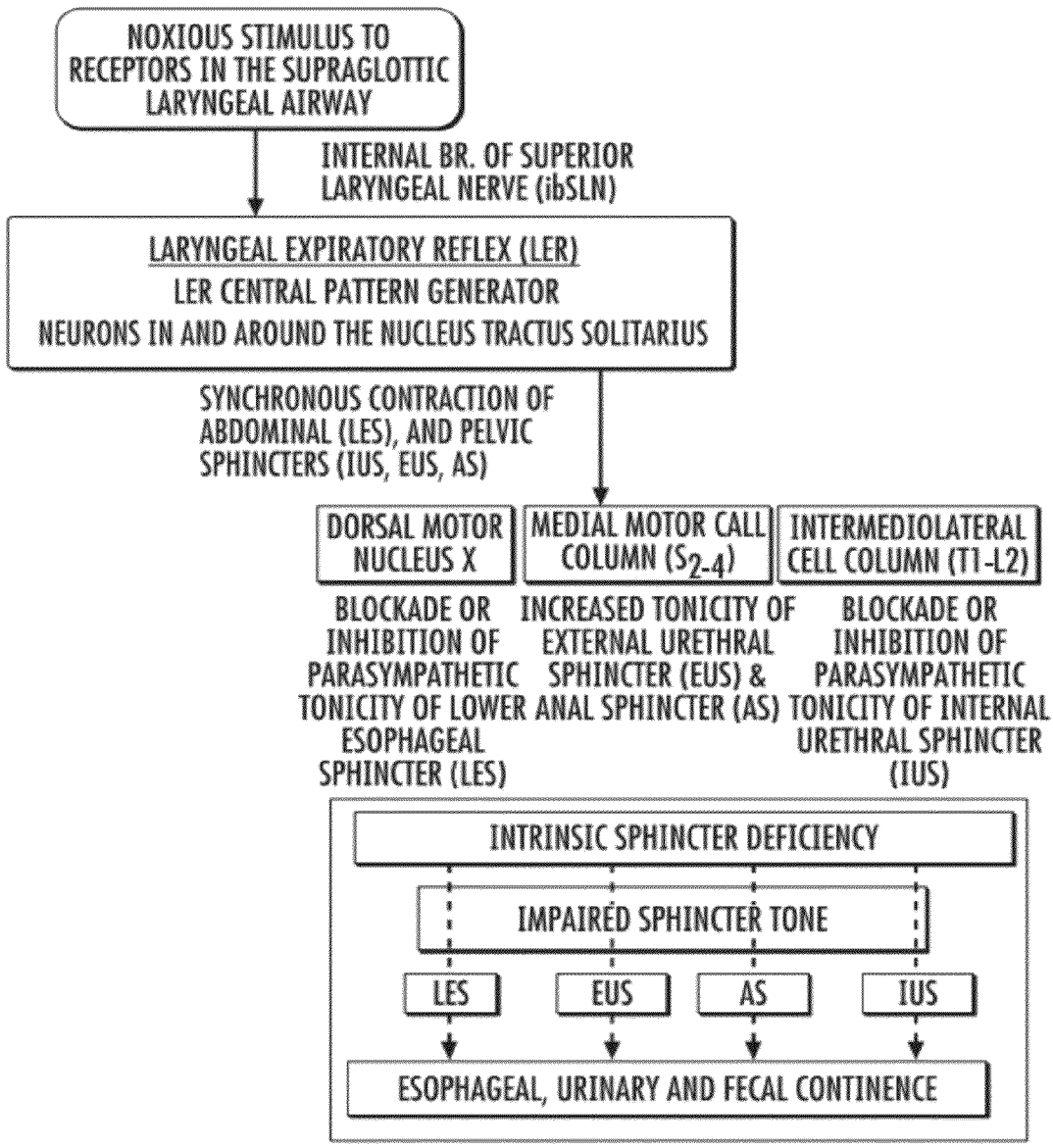
FIG. 23 is a block diagram showing an outline of the laryngeal expiratory reflex (LER) and results with the intrinsic sphincter deficiency and esophageal, urinary and fecal continence.

FIG. 23 is a block diagram showing a laryngeal expiratory reflex (LER) flow and indicates the different effects from activation such as the dorsal motor nucleus X; the medial motor cell column; and intermediolateral cell column.

Figure 24A:
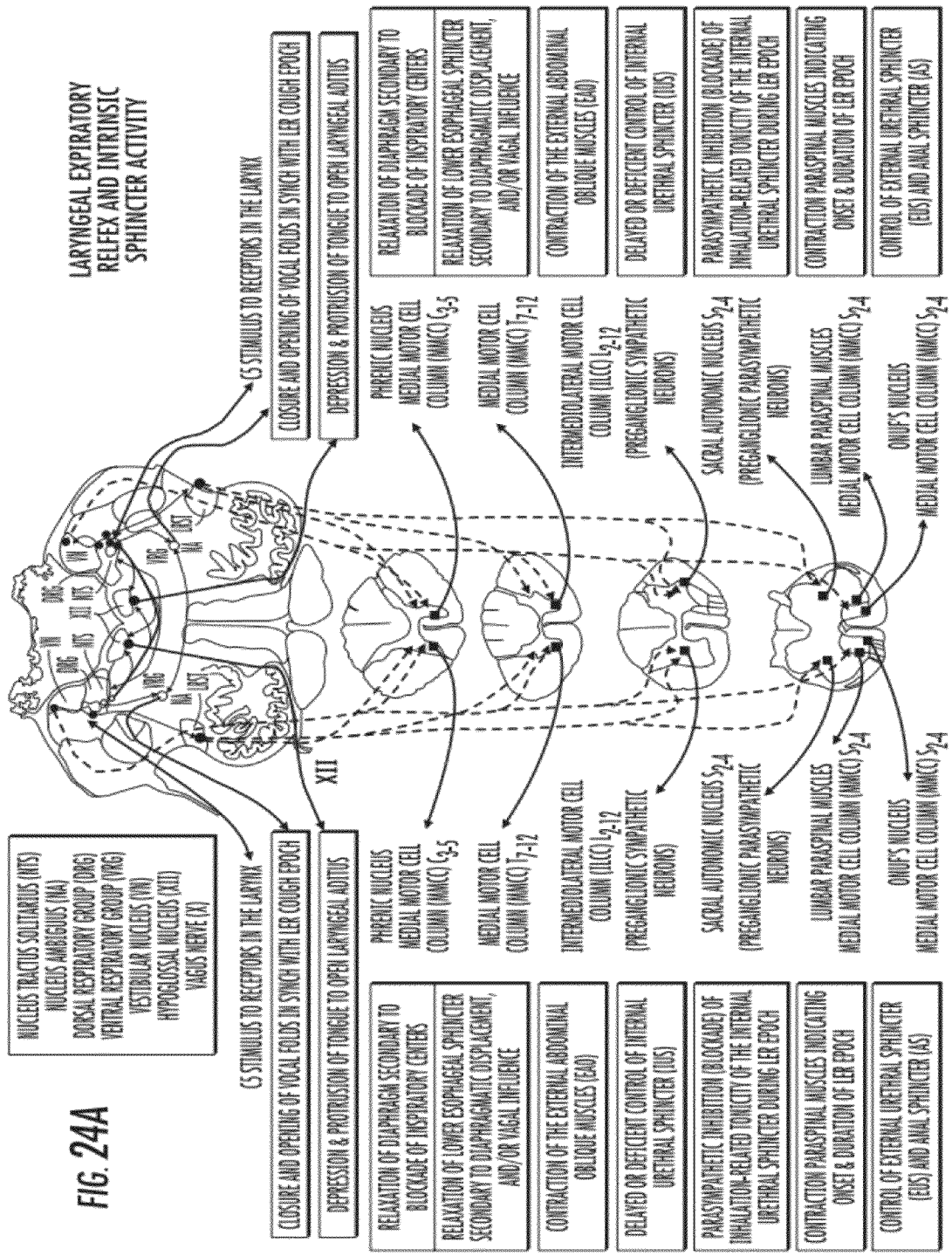

FIG. 24A is a diagram detailing what occurs during the LER (Laryngeal Expiratory Reflex) and Intrinsic Sphincter Activity). This diagram shows a schematic of the LER neural circuits. FIG. 24B illustrates Voluntary Cough (VC) pathways. There are some key points regarding VC, micturition, and the brainstem mediated LER.

This application is related to copending patent applications entitled, "SYSTEM AND METHOD FOR TESTING THE GASTRIC VALVE," which is filed on the same date and by the same assignee and inventors, the disclosure which is hereby incorporated by reference.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A method of testing the gastric valve and urethral sphincter in a patient, comprising:
   administering a contrast agent into the esophagus of a patient followed by;
   inducing an involuntary reflex cough epoch within the patient to isolate the gastric valve from the lower esophageal sphincter (LES) and isolate the external urethral sphincter from the internal urethral sphincter;
   detecting using an imaging sensor the flow of the contrast agent during the involuntary reflex cough epoch and determining whether stomach reflux occurred indicative of a malfunctioning gastric valve;
   determining if urine leaked indicative of stress urinary incontinence (SUI);
   inserting a urinary catheter having a pressure sensor within the bladder;
   obtaining an electromyogram (EMG) from involuntary cough activated intercostals and/or paraspinals; and
   processing, using a processor, the data from the pressure sensor with the EMG to estimate the severity of the SUI.

2. The method according to claim 1, further comprising detecting the flow of contrast agent at the level of the LES.

3. The method according to claim 1, wherein the imaging sensor comprises a fluoroscopic instrument configured to image the contrast agent.

4. The method according to claim 1, further comprising introducing a chemo-irritant for inducing the involuntary reflex cough epoch.

5. The method according to claim 1, further comprising administering Barium sulfate as the contrast agent.

6. The method according to claim 1, further comprising administering the contrast agent by having the patient swallow the contrast agent.

7. The method according to claim 1, further comprising inducing the involuntary reflex cough epoch immediately following the administration of the contrast agent.

8. The method according to claim 1, further comprising positioning the patient in a semi-recumbent lithotomy position when inducing the involuntary reflex cough epoch.

9. A method of testing the gastric valve and urethral sphincter in a patient, comprising:

administering a contrast agent into the esophagus of a patient followed by;

inducing an involuntary reflex cough epoch within the patient to isolate the gastric valve from the lower esophageal sphincter (LES) and isolate the external urethral sphincter from the internal urethral sphincter;

detecting using an imaging sensor the flow of the contrast agent during the involuntary reflex cough epoch and determining whether stomach reflux occurred indicative of a malfunctioning gastric valve;

determining if urine leaked indicative of stress urinary incontinence (SUI);

inserting a urinary catheter having a pressure sensor within the bladder;

obtaining an electromyogram (EMG) from the involuntary cough activated intercostals and/or paraspinals; and processing, using a processor, the data from the pressure sensor with the EMG to estimate the severity of the SUI; and measuring the amount of reflux that occurs during the involuntary reflex cough epoch to estimate the severity of the malfunctioning gastric valve.

10. The method according to claim 9, further comprising measuring the amount of reflux that occurs during the involuntary reflex cough epoch using a Ng/Og catheter.

11. The method according to claim 9, further comprising measuring the amount of reflux that occurs during the involuntary reflex cough epoch by comparing a plurality of photomontages taken by the image sensor during the involuntary reflex cough epoch.

12. The method according to claim 9, further comprising detecting the flow of contrast agent at the level of the LES.

13. The method according to claim 9, wherein the imaging sensor comprises a fluoroscopic instrument configured to image the contrast agent.

14. The method according to claim 9, further comprising introducing a chemo-irritant for inducing the involuntary reflex cough epoch.

15. The method according to claim 9, further comprising administering Barium sulfate as the contrast agent.

16. The method according to claim 9, further comprising administering the contrast agent by having the patient swallow the contrast agent.

17. The method according to claim 9, further comprising inducing the involuntary reflex cough epoch immediately following the administration of the contrast agent.

18. The method according to claim 9, further comprising positioning the patient in a semi-recumbent lithotomy position when inducing the involuntary reflex cough epoch.

19. A system for testing the gastric valve and urethral sphincter in a patient, comprising:

a contrast agent that is administered into the esophagus of a patient;

a nebulizer containing a chemo-irritant agent that induces an involuntary reflex cough epoch within the patient after administration of the contrast agent to the patient in order to isolate the gastric valve from the lower esophageal sphincter (LES) and isolate the external urethral sphincter from the internal urethral sphincter;

an imaging sensor positioned adjacent to the patient and configured to detect and display the flow of the contrast agent during the involuntary cough epoch such that reflux from the stomach that occurs during the involuntary reflex cough epoch is displayed indicative of a malfunctioning gastric valve;

a urine leakage detector configured to detect urine leakage during the involuntary reflex cough epoch indicative of stress urinary incontinence (SUI);

a urinary catheter having a pressure sensor within the bladder;

at least one electromyogram pad configured for obtaining an electromyogram (EMG) from the involuntary cough activated intercostals and/or paraspinals; and a processor configured to receive data from the pressure sensor and EMG and estimate the severity of the SUI.

20. The system according to claim 19, wherein the imaging sensor is positioned to detect the flow of contrast agent at the level of the LES.

21. The system according to claim 19, wherein the imaging sensor comprises a fluoroscopic instrument configured to image the contrast agent.

22. The system according to claim 19, wherein the chemo-irritant agent comprises a composition of L-tartrate in a pharmaceutically acceptable carrier.

23. The system according to claim 19, wherein the contrast agent comprises Barium sulfate.

24. The system according to claim 19, and further comprising a Ng/Og catheter configured to measure the amount of reflux that occurs during the involuntary reflex cough epoch wherein the measured amount of reflux is indicative of an estimate of the severity of the malfunctioning gastric valve.

25. The system according to claim 19, and further comprising a platform that supports the patient, said imaging sensor mounted to the platform in a position to image the flow of contrast through the esophagus at the LES, and a movable support arm and swivel adapter mounting the nebulizer.

26. The system according to claim 19, and further comprising a processor connected to the imaging sensor that receives imaging data from the imaging sensor regarding the flow of contrast agent and reflux and configured to process the data and determine severity of the malfunctioning gastric valve.

27. The system according to claim 19, wherein the urine leakage detector comprises a urinary catheter.

* * * * *